US011626000B2

(12) United States Patent
Durlach et al.

(10) Patent No.: US 11,626,000 B2
(45) Date of Patent: *Apr. 11, 2023

(54) PATIENT CARE SYSTEM

(71) Applicant: Stryker Corporation, Kalamazoo, MI (US)

(72) Inventors: Thomas Joseph Durlach, Kalamazoo, MI (US); Ross Michael Nave, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/854,046

(22) Filed: Jun. 30, 2022

(65) Prior Publication Data

US 2022/0335803 A1 Oct. 20, 2022

Related U.S. Application Data

(63) Continuation of application No. 17/354,633, filed on Jun. 22, 2021, now Pat. No. 11,410,524, which is a (Continued)

(51) Int. Cl.
*G08B 21/04* (2006.01)
*A61G 7/012* (2006.01)
(Continued)

(52) U.S. Cl.
CPC ........ *G08B 21/0461* (2013.01); *A61B 5/1115* (2013.01); *A61B 5/4809* (2013.01); *A61B 5/746* (2013.01); *A61G 7/012* (2013.01);
*A61G 7/018* (2013.01); *A61G 7/0527* (2016.11); *A61G 7/0528* (2016.11); *G08B 21/0415* (2013.01);
(Continued)

(58) Field of Classification Search
None
See application file for complete search history.

(56) References Cited

U.S. PATENT DOCUMENTS

2011/0205061 A1* 8/2011 Wilson ................. G16H 40/20
340/573.1
2014/0080413 A1* 3/2014 Hayes ..................... H04B 5/02
455/41.1

(Continued)

*Primary Examiner* — John F Mortell
(74) *Attorney, Agent, or Firm* — Warner Norcross + Judd LLP

(57) ABSTRACT

A patient support apparatus system and patient support apparatus, such as a bed, cot, stretcher, operating table, recliner, or the like, include a litter frame, a support deck, a sensor configured to detect caregiver activity, a transceiver communicating with a server, and a controller. The controller is configured to send alerts or messages to the server when caregiver assignment errors or caregiver inattention issues are identified. An alert is sent when a caregiver has not attended to a patient within a certain period of time, or when a caregiver has not been assigned to a particular patient or a particular location within a healthcare facility to which a patient has been assigned. The patient support apparatus and system are in communication with other healthcare facility systems and devices that gather and share information and data to alert caregivers in an effort to avoid patient neglect.

20 Claims, 11 Drawing Sheets

Related U.S. Application Data continuation of application No. 16/832,760, filed on Mar. 27, 2020, now Pat. No. 11,062,585.

(60) Provisional application No. 62/826,097, filed on Mar. 29, 2019.

(51) Int. Cl.
*A61G 7/05* (2006.01)
*A61B 5/11* (2006.01)
*A61B 5/00* (2006.01)
*A61G 7/018* (2006.01)

(52) U.S. Cl.
CPC ...... *A61G 2203/12* (2013.01); *A61G 2203/36* (2013.01)

(56) References Cited

U.S. PATENT DOCUMENTS

| | | | |
|---|---|---|---|
| 2014/0266642 A1* | 9/2014 | Girardeau | G16Z 99/00 340/286.07 |
| 2016/0038361 A1* | 2/2016 | Bhimavarapu | H04B 7/24 398/115 |
| 2016/0136356 A1* | 5/2016 | Ribble | A61B 5/0816 705/2 |
| 2016/0183864 A1* | 6/2016 | Kusens | A61B 5/11 340/573.1 |
| 2017/0196743 A1* | 7/2017 | Wiggermann | A61G 7/018 |
| 2018/0146906 A1* | 5/2018 | Harmeyer | A61B 5/11 |
| 2018/0214091 A1* | 8/2018 | Baker | A61B 5/746 |

* cited by examiner

PATIENT CARE SYSTEM

CROSS-REFERENCE TO RELATED APPLICATIONS

This application claims priority to U.S. patent application Ser. No. 17/354,633 filed Jun. 22, 2021, by inventors Thomas Durlach et al. and entitled PATIENT CARE SYSTEM, which in turn claims priority to U.S. patent application Ser. No. 16/832,760 filed Mar. 27, 2020, by inventors Thomas Durlach et al. and entitled PATIENT CARE SYSTEM, which in turn claims priority to U.S. provisional patent application Ser. No. 62/826,097 filed Mar. 29, 2019, by inventors Thomas Durlach et al. and entitled PATIENT CARE SYSTEM, the complete disclosures of all of which are incorporated herein by reference.

BACKGROUND

The present disclosure relates to patient support apparatuses, such as, but not limited to, beds, cots, stretchers, recliners, chairs, and the like; and more particularly to a patient support apparatus system that monitors caregiver-to-patient assignments, caregiver activities at the patient support apparatus, and/or other caregiving activities and sends an alert if there is a patient with no caregiver assigned, or if a patient has not been attended to as expected.

Operation of a healthcare facility, such as a hospital, outpatient facility, or assisted living home, requires numerous workers skilled in providing healthcare. Proper staffing and assignment of doctors, nurses, and other caregivers is an important factor in delivering quality care to the patients. Caregivers are typically assigned a specific patient, patient support apparatus, or room within the healthcare facility. These assignments can be based on various factors including the availability of caregivers, qualifications of available caregivers, the number of available beds in the unit, the current utilization of the beds in the unit, the existing responsibilities of the caregivers, and the like. Despite the various systems utilized within the healthcare facility aimed at preventing sub-par patient care, the assigned caregiver may not perform the patient care in a timely manner, or a caregiver assignment error can occur and a patient may not be assigned a caregiver and may be overlooked or neglected. Caregiver assignments are further complicated if a patient is moved or transported to another location within the healthcare facility. In some cases, a patient may be "lost" or unaccounted for.

SUMMARY

In its various embodiments, the present disclosure provides a patient care system configured to help healthcare facility staff, including doctors, nurses, and technicians, reduce or avoid caregiver assignment errors and caregiver inattention issues. The system generates and issues an alert when such errors or issues are identified. In some embodiments, an alert may be issued when a patient has not been attended to by a caregiver within a period of time greater than a certain period. In other embodiments, an alarm may be issued when a caregiver has not been assigned to a particular location within the healthcare facility, generally a hospital or treatment room or bay, to which a patient has been assigned. The patient support apparatus can communicate with multiple other healthcare facility systems and devices that gather and share data to aid caregivers in avoiding patient neglect. These and/or other features are disclosed in the various embodiments discussed herein.

According to one embodiment of the present disclosure, a patient support apparatus is provided that includes a litter frame, a support deck supported on the litter frame and adapted to support a patient thereon, and a sensor configured to detect caregiver activity. The patient support apparatus also includes a transceiver, a timer, and a controller. The transceiver communicates with a server and the controller communicates with the sensors, the timer, and the transceiver. The controller is configured to send a caregiver inactivity message to the server when caregiver activity has not been detected for a period of time greater than a predetermined period of time.

In some embodiments, the patient support apparatus includes a caregiver control panel, and detecting caregiver activity includes detecting when any controls on the caregiver control panel are touched or otherwise activated.

According to some embodiments, the caregiver control panel includes controls for raising and lowering the litter frame, changing the position of a section of the support deck, activating and deactivating a brake, controlling a patient support apparatus exit alert, taking a weight reading, locking out one or more functions, setting an alert, and any combination of these controls and the like.

In some embodiments, the predetermined period of time for detecting caregiver activity is received from the server via the transceiver. In other embodiments, the predetermined period of time is input or received by the controller from a caregiver control panel coupled to the patient support apparatus or an electronic medical records (EMR) server.

According to some embodiments, the sensor is adapted to detect audio communication between the patient and a remotely located caregiver. The audio communication takes place via a nurse call communication module typically coupled to the patient support apparatus.

In some embodiments, the patient support apparatus includes a clock, and the predetermined period of time is based on the time of day.

In other embodiments, the patient support apparatus includes a sleep sensor adapted to sense a patient's sleep state and to communicate such with the controller. In such embodiments, the predetermined period of time may be based on the patient's sensed sleep state.

According to still other embodiments, the patient support apparatus includes a patient control panel and a caregiver control panel. The controller is adapted to detect caregiver activity any time a control on the caregiver control panel is activated, yet the controller does not detect caregiver activity when the patient control panel is activated. The patient support apparatus may include more than one patient control panel and more than one caregiver control panel.

In some embodiments, the patient support apparatus includes a patient presence sensor configured to detect the presence of a patient on the support deck. The patient presence sensor is in communication with the controller.

According to some embodiments, the predetermined period of time varies based on whether the patient's presence is sensed or not on the patient support apparatus.

According to still other embodiments, a caregiver inactivity message is not sent if a patient is not present on the support deck when the predetermined period of time expires.

In still other embodiments, the predetermined period of time does not start until a patient's presence is detected on the support deck.

According to another embodiment of the present disclosure, a patient support apparatus is provided that includes a litter frame, a support deck supported on the litter frame and adapted to support a patient thereon, and a caregiver control panel having a plurality of caregiver controls adapted to be activated by a caregiver. The patient support apparatus further includes a transceiver adapted to communicate with a server and a controller in communication with the caregiver control panel and the transceiver. The controller is adapted to send a caregiver activity message to the server in response to one or more of the caregiver controls being activated.

In another embodiment, the controller is adapted to send a caregiver activity message in response to a caregiver communicating with the patient via a nurse call speaker that is communicatively coupled to the patient support apparatus.

In some embodiments, a caregiver activity message is sent to the server each time any of the caregiver control panels are activated. In other embodiments, only a single caregiver activity message is sent to the server for multiple caregiver control panel activations if the multiple activations occur within a predetermined period of time.

In some embodiments, the controller is adapted to send a caregiver inactivity message to the server when the caregiver control panel has not been activated within a predetermined time period.

According to some embodiments, the predetermined period of time for detecting caregiver activity is received by the controller from a patient support apparatus server, the caregiver control panel, or an electronic medical records (EMR) server.

According to another embodiment of the present disclosure, a patient support apparatus system is provided that includes a litter frame, a support deck supported on the litter frame and adapted to support a patient thereon, a sensor adapted to detect a presence of the patient, a transceiver, and a controller in communication with the sensor and the transceiver. The patient support apparatus system further includes a server in communication with the patient support apparatus and the controller via the transceiver. The server is also in communication with a caregiver assignment server that stores caregiver assignments to locations within the healthcare facility. Further, the server is configured to receive location data regarding a current location of the patient support apparatus. The server is adapted to determine if a caregiver has been assigned to the current location of the patient support apparatus, and to issue an alert if the server determines that a caregiver has not been assigned to the current location of the patient support apparatus.

In some embodiments, an alert is not sent if a patient is not determined by the sensor to be present on the support deck.

According to some embodiments, the patient support apparatus includes a location detector adapted to receive a location identifier from a fixed locator when the patient support apparatus is positioned adjacent the fixed locator.

In some embodiments, the current location of the patient support apparatus is a room within the healthcare facility.

In other embodiments, the server is configured to request the caregiver assignment from the caregiver assignment server whenever the current location of the patient support apparatus changes. Additionally, or alternatively, the server is configured to request the caregiver assignment from the caregiver assignment server whenever a caregiver assignment changes.

According to another embodiment, the server is configured to receive caregiver location data from a real time locating and tracking server indicating the locations of caregivers within the healthcare facility. The server is also adapted to use the location data to determine if a caregiver has visited a location, corresponding to the location identifier, within the healthcare facility within the predetermined amount of time. The server issues an inactivity alert if a caregiver has not visited the location within the predetermined amount of time.

In some embodiments, the server is in communication with an electronic medical records (EMR) server that stores patient records. The server retrieves the patient record from the EMR server for the patient associated with the patient support apparatus and determines if updates to the patient record have occurred within a predetermined amount of time. The server issues an inactivity alert if the patient record has not been updated within the predetermined amount of time.

According to some embodiments, the patient support apparatus includes a timer in communication with the controller. The controller sends a caregiver inactivity message to the server when caregiver activity has not been detected for a period of time greater than a predetermined period of time.

In some embodiments, the patient support apparatus includes a caregiver control panel in communication with the controller. The controller is adapted to send a caregiver activity message to the server in response to any one or more of the caregiver controls being activated.

According to another embodiment of the present disclosure, a patient support apparatus system is provided that includes a litter frame, a support deck supported on the litter frame and adapted to support a patient thereon, a sensor adapted to detect a presence of the patient, a transceiver, and a controller in communication with the sensor and the transceiver. The patient support apparatus system further includes a server in communication with the patient support apparatus via the transceiver. The server is also in communication with an admission/discharge/tracking (ADT) server that stores patient location information. The server receives location data regarding a current location of the patient to determine if a caregiver has been assigned to the current location of the patient. The server issues an alert if the server determines that a caregiver has not been assigned to the current location of the patient.

According to another embodiment of the present disclosure, a patient support apparatus system is provided that includes a litter frame, a support deck supported on the litter frame and adapted to support a patient thereon, a sensor adapted to detect a presence of the patient, a transceiver, and a controller in communication with the sensor and the transceiver. The patient support apparatus system further includes a server in communication with the patient support apparatus via the transceiver. The server is also in communication with an electronic medical records (EMR) server that stores patient records. The server retrieves a particular patient record from the EMR server corresponding to the patient to determine if updates to the particular patient record have occurred within a predetermined amount of time. The server also issues an inactivity alert if the particular patient record has not been updated within the predetermined amount of time.

In some embodiments, the inactivity alert is not issued or sent if a patient is not present on the support deck.

According to some embodiments, the patient support apparatus includes a location detector adapted to receive a location identifier from a fixed locator when the patient support apparatus is positioned adjacent the fixed locator. The server may also receive caregiver location data from a real time locating and tracking server indicating locations of caregivers within the healthcare facility. The server uses the location data to determine if a caregiver has visited a location, corresponding to the location identifier, within the healthcare facility within the predetermined amount of time. The server issues an inactivity alert if a caregiver has not visited the location corresponding to the location identifier within the predetermined amount of time.

In still other embodiments, the server is in communication with an admission/discharge/tracking (ADT) server that stores patient location information. The server receives location data regarding a current location of the patient to determine if a caregiver has been assigned to the current location of the patient. The server issues an alert if the server determines that a caregiver has not been assigned to the current location of the patient.

According to other embodiments, the server is configured to determine if a particular patient record includes a prescribed event to occur within a prescribed time. The server monitors whether the prescribed event occurs at the prescribed time, and issues an inactivity alert if the prescribed event does not occur within the prescribed time.

In some embodiments, the prescribed event includes performing a therapy utilizing a mattress supported on the support deck. The server receives status data from the patient support apparatus indicating when the therapy is performed and utilizes the status data to determine if the prescribed event is performed within the prescribed time.

In other embodiments, the prescribed event includes performing an activity that is to be documented to the particular patient record stored at the EMR server. The server is configured to request an updated particular patient record from the EMR server to determine if the prescribed event is performed within the prescribed time.

In some embodiments, the activity includes visiting the patient at a regular time interval. In other embodiments, the activity includes taking a weight reading of the patient. In still other embodiments, the activity includes performing a fall risk assessment of the patient or performing a bed sore risk assessment of the patient.

According to still another embodiment of the present disclosure, a patient support apparatus system is provided that includes a litter frame, a support deck supported on the litter frame and adapted to support a patient thereon, and a location detector adapted to receive a location identifier from a fixed locator when the patient support apparatus is positioned adjacent the fixed locator. The patient support apparatus system also includes a transceiver, a controller adapted to transmit the location identifier, and a server adapted to receive the location identifier from the patient support apparatus and correlate the location identifier with a location within the healthcare facility. The server receives caregiver location data from a real time locating and tracking server, indicating locations of caregivers within the healthcare facility. The server uses the location data to determine if a caregiver has visited a location, corresponding to the location identifier, within the healthcare facility within a predetermined amount of time. Further, the server issues an inactivity alert if a caregiver has not visited the location corresponding to the location identifier within the predetermined amount of time.

In some embodiments, the locating and tracking server tracks a caregiver location badge worn by the caregiver.

Before the various embodiments disclosed herein are explained in detail, it is to be understood that the claims are not to be limited to the details of operation, to the details of construction, or to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
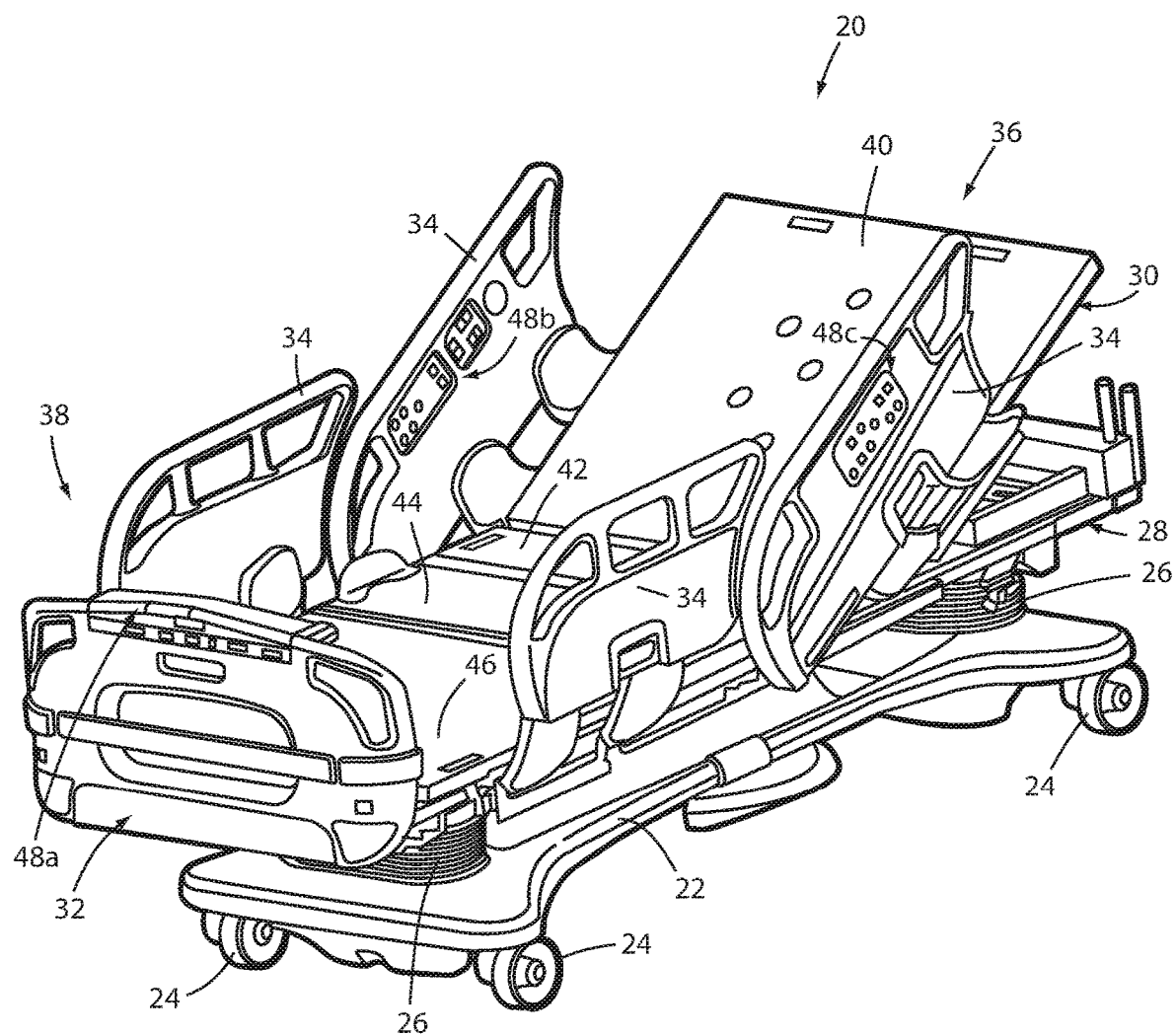
FIG. 1 is perspective view of a patient support apparatus into which one or more of the features of the present disclosure may be incorporated.

A patient care system 106 according to one embodiment of the present disclosure includes a patient support apparatus 20, such as the patient support apparatus 20 which is shown in FIG. 1. Although the particular form of patient support apparatus 20 illustrated in FIG. 1 is a bed adapted for use in a hospital or other medical setting, it will be understood that the patient support apparatus 20 could, in different embodiments, be a cot, a stretcher, a gurney, a recliner, or any other structure capable of supporting a patient that may be used during times when the patient is not accompanied by a caregiver. For purposes of the following written description, the patient support apparatus 20 will be described as a bed with the understanding the following written description applies to these other types of patient support apparatuses.

In general, the patient support apparatus 20 includes a base 22 having a plurality of wheels 24, a lift subsystem comprising a pair of lifts 26 supported on the base, a litter frame 28 supported on the lifts 26, and a support deck 30 supported on the litter frame 28. Patient support apparatus 20 further includes a headboard (not shown), a footboard 32, and a plurality of siderails 34. Siderails 34 are all shown in a raised position in FIG. 1 but are each individually movable to a lower position in which ingress into, and egress out of, patient support apparatus 20 is not obstructed by the lowered siderails 34. In some embodiments, the siderails 34 may be moved to one or more intermediate positions as well.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 36 and a foot end 38, each of whose height can be independently adjusted by the nearest lift 26. The patient support apparatus 20 is designed so that when an occupant lies thereon, his or her head will be positioned adjacent head end 36 and his or her feet will be positioned adjacent foot end 38.

Litter frame 28 provides a structure for supporting support deck 30, the headboard, footboard 32, and siderails 34. Support deck 30 provides a support surface for a mattress (not shown in FIG. 1), or other soft cushion, so that a person may lie and/or sit thereon. The support deck 30 is made of a plurality of sections, some of which are pivotable about generally horizontal pivot axes. In the embodiment shown in FIG. 1, the support deck 30 includes a head section 40, a seat section 42, a thigh section 44, and a foot section 46. Head section 40, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 44 and foot section 46 may also be pivotable about generally horizontal pivot axes.

Patient support apparatus 20 further includes a plurality of user interfaces or control panels 48 that enable a user of patient support apparatus 20, such as a patient and/or an associated caregiver, to control one or more aspects of patient support apparatus 20. In the embodiment shown in FIG. 1, patient support apparatus 20 includes a footboard control panel 48a, a pair of inner siderail patient control panels 48b (only one of which is visible), and a pair of outer siderail caregiver control panels 48c (only one of which is visible). Footboard control panel 48a and outer siderail control panels 48c are intended to be used by caregivers, or other authorized personnel, while inner siderail control panels 48b are intended to be used by the patient associated with patient support apparatus 20. Not all of the control panels 48 include the same controls and/or functionality. In the illustrated embodiment, footboard control panel 48a includes a substantially complete set of controls for controlling patient support apparatus 20 while control panels 48b and 48c include a selected subset of those controls. Control panels 48 may include controls for allowing a user to do one or more of the following: change a height of support deck 30, raise or lower head section 40, activate and deactivate a brake for wheels 24, arm an exit detection system, take a weight reading of the patient, activate and deactivate a propulsion system, and communicate with a healthcare facility computer network installed in the healthcare facility in which patient support apparatus 20 is positioned. Inner siderail control panels 48b may also include a nurse call control that enables a patient to call a nurse. A speaker and microphone are included in order to allow the patient to orally communicate with the remotely positioned nurse.

Footboard control panel 48a is shown implemented in FIG. 1 as having a plurality of individual controls. These controls may be implemented as buttons, dials, switches, or other devices. Any of control panels 48a-c may also include a display for displaying information regarding patient support apparatus 20. The display may be a touchscreen in some embodiments.

The mechanical construction of those aspects of patient support apparatus 20 not explicitly described herein may be the same as, or nearly the same as, the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that those aspects of patient support apparatus 20 not explicitly described herein can alternatively be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of those aspects of patient support apparatus 20 not explicitly described herein may also take on forms different from what is disclosed in the aforementioned references.

Figure 2:
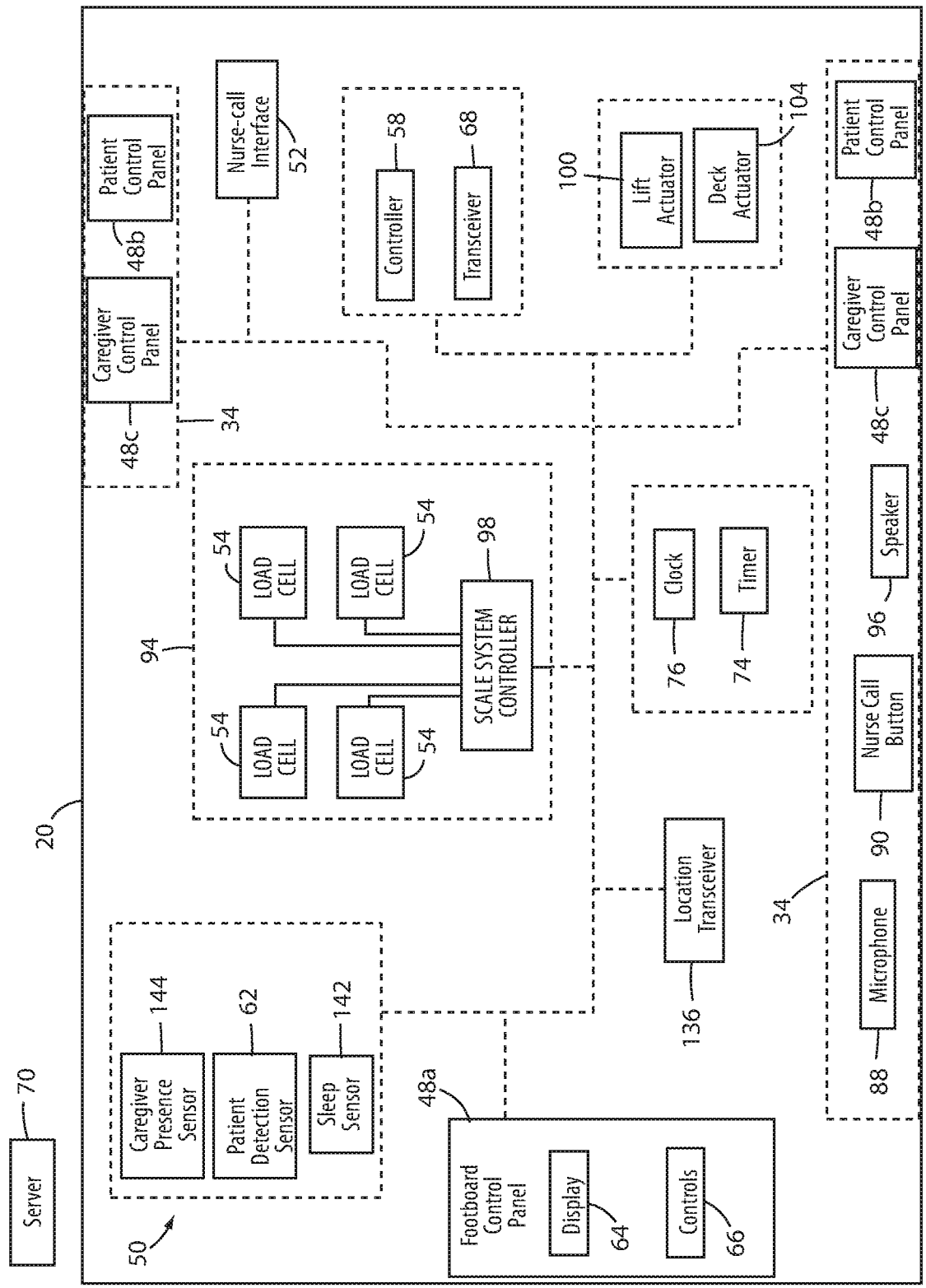
FIG. 2 is a diagram of one embodiment of a control system that may be used with the patient support apparatus of FIG. 1, or with any of the other patient support apparatus embodiments described herein.

Referring now to FIG. 2, patient support apparatus 20 includes a control system 50 comprising a plurality of control panels 48a-c, a plurality of actuators 100, 104, a controller 58, a transceiver 68, a timer 74, a clock 76, one or more sensors 62, 142, 144, a nurse call button 90, a scale/exit detection system 94, a microphone 88, and a speaker 96. Scale/exit detection system 94 is used to detect the weight of an occupant of the patient support apparatus 20 and/or as an exit detection system. The particular structural details of scale/exit detection system 94 can vary widely. In the embodiment shown in FIG. 2, scale/exit detection system 94 includes a plurality of load cells 54 and a scale/exit detection system controller 98 adapted to process the outputs from the load cells to determine a weight of the patient and/or to determine when the patient has exited, or is about to exit, from support deck 30. In some embodiments, load cells 54 may be replaced with linear variable displacement transducers and/or any one or more capacitive, inductive, and/or resistive transducers that are configured to produce a changing output in response to changes in the force exerted against them. Still other types of forces sensors may be used with patient support apparatus 20.

Load cells 54 are configured to support litter frame 28. More specifically, load cells 54 are configured such that they provide complete mechanical support for litter frame 28 and all of the components that are supported on litter frame 28

(e.g. support deck 30, footboard 32, the headboard, siderails 34, etc.). Because of this construction, load cells 54 detect the weight of not only those components of patient support apparatus 20 that are supported by litter frame 28 (including litter frame 28 itself), but also any objects or persons who are wholly or partially being supported by support deck 30. Load cells 54 are adapted to detect downward forces exerted by an occupant of support deck 30. Thus, when an occupant is positioned on support deck 30 and substantially still (i.e. not moving in a manner involving accelerations that cause forces to be exerted against support deck 30), load cells 54 detect the weight of the occupant (as well as the weight of any components of patient support apparatus 20 that are supported—directly or indirectly—by load cells 54).

When functioning as a scale system, the outputs of the load cells 54 are summed by processor 98 to detect a weight of the occupant. When functioning as an exit detection system, the outputs of the load cells 54 are read and used to detect when an occupant has exited the apparatus 20, or when an occupant may be about to exit the apparatus 20. One exemplary scale/exit detection system 94 is described in U.S. Patent Application Pub. No. 2017/0003159, filed on Jun. 17, 2016, entitled PERSON SUPPORT APPARATUS WITH LOAD CELLS, which is hereby incorporated by reference herein in its entirety. Another exemplary exit detection system is described in U.S. Pat. No. 5,276,432, filed on Jan. 15, 1992, entitled PATIENT EXIT DETECTION MECHANISM FOR HOSPITAL BED, which is hereby incorporated by reference herein in its entirety. Other types of scale and/or exit detection systems may be used.

Actuators 100, 104 of control system 50 are adapted to control the movement of lifts 26 and head section 40, respectively. Actuators 100 and 104 may be linear actuators, rotary actuators, or other types of actuators capable of pivoting head section 40 about a generally horizontal pivot axis or lifting litter frame 28. Actuators 100, 104 may be electrically powered, hydraulic, electro-hydraulic, pneumatic, or the like. Actuators 100, 104 are controlled by one or more controls positioned on one or more of the control panels 48a-48c.

Control system 50 includes, in some embodiments, one or more patient detection sensors 62 that are adapted to detect when a patient is present on support deck 30. In some embodiments, control system 50 omits patient detection sensors 62 and utilizes the outputs of load cells 54 to detect the presence and/or absence of a patient on patient support apparatus 20. In other embodiments, control system omits patient detection sensors 62 altogether and functions as described below without detecting the absence/presence of a patient. In the embodiment shown in FIG. 2, control system 50 includes both patient detection sensors 62 and load cells 54.

When patient detection sensors 62 are included, such sensors 62 may include one or more of a variety of different sensors that are able to detect the absence or presence of the patient on patient support apparatus 20. In some embodiments, sensors 62 are adapted to detect one or more vital signs of the patient when the patient is supported on patient support apparatus 20. In such embodiments, the detection of a patient's vital sign is used as confirmation of the patient's presence, and the absence of a detected vital sign is interpreted as the patient being absent. Several methods and sensors for detecting a patient's vital signs are disclosed in commonly assigned U.S. patent application Ser. No. 62/253,167, filed Nov. 10, 2015, by inventors Marko Kostic et al. and entitled PERSON SUPPORT APPARATUSES WITH ACCELERATION DETECTION, the complete disclosure of which is incorporated herein by reference. A patient's breathing rate and/or heart rate may also be detected using load cells 54, such as is disclosed in commonly assigned U.S. Pat. No. 7,699,784 issued to Wan Fong et al. and entitled SYSTEM FOR DETECTING AND MONITORING VITAL SIGNS, the complete disclosure of which is hereby incorporated herein by reference. Still other methods and/or sensors can be used to detect a patient's vital signs, and thereby determine if a patient is present on patient support apparatus 20 or not.

Detecting a patient's vital signs may also be performed in other manners. For example, in some embodiments, patient presence sensors 62 are incorporated into a mattress, such as the mattress disclosed in commonly assigned U.S. patent application Ser. No. 13/836,813 and 61/697,10, entitled INFLATABLE MATTRESS AND CONTROL METHODS and PATIENT SUPPORT, respectively, the former of which was filed Mar. 15, 2013 and the latter of which was filed Sep. 5, 2012, the complete disclosures of both of which are hereby incorporated herein by reference. When incorporated into a mattress, the sensor 62, in some embodiments, detects respiration and/or heart rates by a pressure sensor included within the mattress that detects fluid pressure changes within one or more bladders contained within the mattress. Such fluid pressure changes are filtered for frequencies within those of the normal heart rate and breathing rate and processed, such as through Fourier analysis, or otherwise, to yield a heart rate and/or respiration rate. In embodiments using the mattress construction disclosed in the above-referenced Ser. No. 13/836,813 and/or 61/697,10 applications, the mattress also includes a plurality of depth sensors that measure the depth which the patient has sunk into the mattress. These depth sensor signals may be combined with the air pressure signals to determine a patient's breathing rate and or heart rate.

In other embodiments, patient detection sensors 62 are implemented to detect the patient's presence/absence in manners that don't involve the detection of vital signs. For example, in some embodiments, patient detection sensors 62 include one or more thermal sensors that detect the absence/presence of the occupant and/or the position of the occupant's head on the personal support apparatus 20. Further details of such a thermal sensing system are disclosed in commonly assigned U.S. patent application Ser. No. 14/692,871 filed Apr. 22, 2015, by inventors Marko Kostic et al. and entitled PERSON SUPPORT APPARATUS WITH POSITION MONITORING, the complete disclosure of which is incorporated herein by reference.

In still other embodiments, patient detection sensors 62 are configured to detect the absence or presence of an occupant using one or more of the methods disclosed in commonly assigned U.S. patent application Ser. No. 14/928,513 filed Oct. 30, 2015, by inventors Richard Derenne et al. and entitled PERSON SUPPORT APPARATUSES WITH PATIENT MOBILITY MONITORING, the complete disclosure of which is also hereby incorporated herein by reference. In still other embodiments, patient detection sensors 62 include one or more video and/or infrared cameras detecting an occupant's presence, absence, and/or position, such as disclosed in commonly assigned U.S. patent application Ser. No. 14/578,630 filed Dec. 22, 2014, by inventors Richard Derenne et al. and entitled VIDEO MONITORING SYSTEM, the complete disclosure of which is also hereby incorporated herein by reference. Such cameras are positioned on the patient support apparatus 20 in some embodiments; position off-board the patient support apparatus 20 in other embodiments; and include both one or more on-board cameras and one or more off-board cameras in still other embodiments.

In yet another alternative embodiment, patient presence sensors 62 sense the presence, absence, and/or position of an occupant using a pressure sensing mat on which, or above which, the patient lies. The pressure sensing mat may be positioned on top of, or underneath, the mattress on support deck 30, such as is disclosed in commonly assigned U.S. patent application Ser. No. 14/003,157 filed Mar. 2, 2012, by inventors Joshua Mix et al. and entitled SENSING SYSTEM FOR PATIENT SUPPORTS, the complete disclosure of which is also incorporated herein by reference. This pressure sensing mat is also able to detect the overall shape of the patient's weight or the object's weight (e.g. the weight footprint) when positioned on the mattress. This overall shape is processed by either controller 58, or a controller within the flexible pressure sensing mat, to determine whether the shape corresponds to a human or an object. The result of this determination is used by controller 58 to distinguish between the objects and humans moving onto or off the patient support apparatus.

In yet another embodiment, patient presence sensors 62 are adapted to detect a bracelet, tag, or other radio-frequency object worn by the patient using one or more near field transceivers incorporated into patient support apparatus 20. Such sensors 62 are able to communicate via near field communication with near field tags, bracelets, etc. worn by the patients. Examples of near field transceivers that may be incorporated into patient support apparatuses and used to detect patient-worn tags, bracelets, etc. are disclosed in commonly assigned U.S. patent application Ser. No. 13/802,992, filed Mar. 14, 2013 by applicants Michael Hayes et al., and entitled COMMUNICATION SYSTEMS FOR PATIENT SUPPORT APPARATUSES, the complete disclosure of which is hereby incorporated herein by reference. Still other types of sensors that detect the patient's presence in other manners may be used.

Control system 50 also includes, in the embodiment shown in FIG. 2, one or more caregiver presence sensors 144. Caregiver presence sensors 144 may take on a variety of different forms. In one embodiment, caregiver presence sensors 144 are one or more near field sensors that are adapted to detect near field cards, tags, or the like that are carried by caregivers. In another embodiment, caregiver presence sensors 144 are RF ID sensors that are adapted to detect RF ID cards, tags, or the like that are worn or carried by caregivers. In still another embodiment, patient support apparatus 20 includes one or more cameras (visible light and/or infrared light) that have fields of view in the areas adjacent patient support apparatus 20 and are able to detect the presence of a caregiver within those fields of view. One example of a patient support apparatus 20 having such cameras built into it is found in commonly assigned U.S. Pat. No. 9,814,410 issued to Kostic et al. and entitled PERSON SUPPORT APPARATUS WITH POSITION MONITORING, the complete disclosure of which is incorporated herein by reference. In still other embodiments, one or more caregiver presence sensors 144 may be incorporated into patient care system 106 that are not positioned on patient support apparatus 20. For example, one or more cameras may be positioned within the room in which patient support apparatus 20 is located and adapted to capture images of the caregivers, when present, and report that information to patient care server 70. One such suitable camera system is disclosed in commonly assigned U.S. Pat. No. 10,121,070 issued to Derenne et al. and entitled VIDEO MONITORING SYSTEM, the complete disclosure of which is incorporated herein by reference. Still other types of caregiver presence detectors 144 may be utilized, either in lieu of, or in addition to, the caregiver presence sensors 144 discussed herein.

Controller 58 is constructed of any electrical component, or group of electrical components, that are capable of carrying out the functions described herein. In many embodiments, controller 58 is a conventional microcontroller, although not all such embodiments need include a microcontroller. In general, controller 58 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 58 in carrying out the functions described herein, as well as the data necessary for carrying out these functions, are stored in a memory (not labeled) accessible to controller 58.

Controller 58 is in communication with footboard control panel 48*a*, as shown in FIG. 2. Controller 58 also communicates with the inner siderail control panels 48*b* and the outer siderail control panels 48*c* that are positioned on patient support apparatus 20. Footboard control panel 48*a* and outer siderail control panels 48*c* are intended to be used by caregivers, while inner siderail control panels 48*b* are intended to be used by a patient.

Each of the control panels 48*a-c* includes a plurality of controls 66 for controlling various functions of the patient support apparatus 20. One or more of the controls panels 48*a-c* may also or alternatively include a display 64. When included, display 64 is a touch screen display in at least some embodiments, although it will be understood that a non-touch screen display 64 may alternatively be used. It will also be understood that any of the control panels 48*a-c* may be implemented without any display at all. Controls 66 can be touch sensitive controls that may be physically implemented in a variety of different manners. In some embodiments, controls 66 are implemented as capacitive sensors positioned adjacent display 64 that capacitively detect when a user presses them. In other embodiments, controls 66 are implemented as buttons, switches, or other types of force or touch-sensitive devices. In still other embodiments, one or more of controls 66 may be incorporated into touchscreen display 64. Still other variations are possible.

The controls 66 of control panels 48*a-c* include controls for raising/lowering the litter frame 28, changing the position of a section 40-46 of the support deck 30, activating/deactivating a brake, controlling scale/exit detection system 94 (e.g. taking a weight reading, arming the exit detection system 94, etc.), locking out one or more functions, setting an alert, inputting patient information and/or therapy data (e.g. a prescribed turning frequency, etc.), and/or other controls. At least one of the inner control panels 48*b* also include the nurse call button 90, speaker 96, and microphone 88 which collectively enable the patient to call and talk to a remotely positioned nurse, such as a nurse located at a corresponding nurses' station within the healthcare facility.

Patient support apparatus 20 communicates with a healthcare facility network 72 via transceiver 68 (FIG. 2). In some embodiments, transceiver 68 is a wireless transceiver adapted to communicate with one or more wireless access points 80 of the healthcare facility's local area network 72. In such embodiments, transceiver 68 may be a WiFi transceiver. In other embodiments, transceiver 68 may be a wired transceiver that communicates with network 72 over a wired network, such as an Ethernet cable or the like. Regardless of whether transceiver 68 is a wired or wireless transceiver, it enables controller 58 to communicate with one or more servers on the healthcare facility's network 72, such as, but not limited to, a patient support apparatus server 132.

Figure 3:
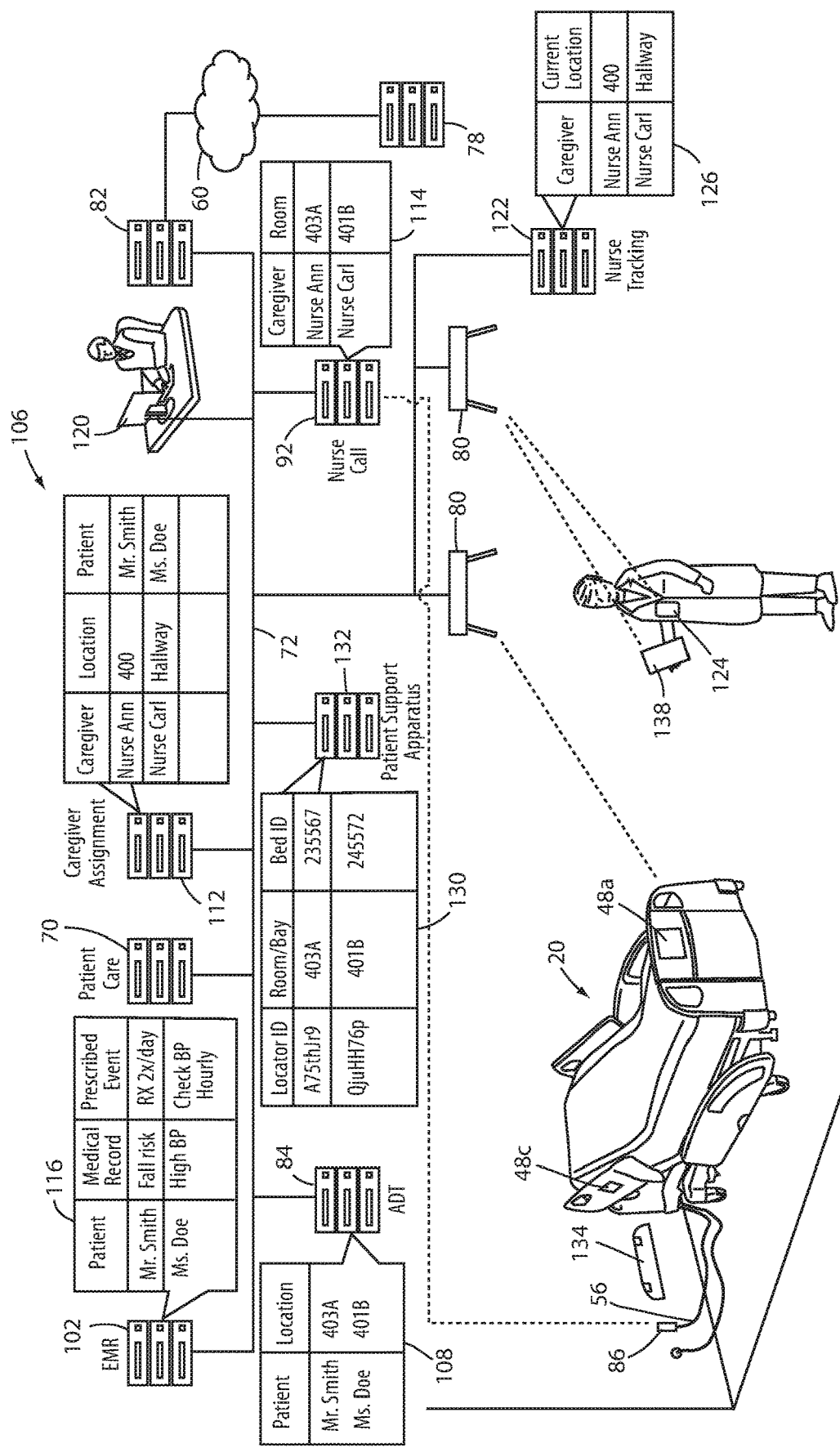
FIG. 3 is a diagram of the hardware and data structures used in a patient care system according to one aspect of the present disclosure.

Control system 50 of patient support apparatus 20 also includes a nurse-call interface 52 (FIG. 2) for communicatively coupling patient support apparatus 20 to a conventional nurse call system. Conventional nurse call systems typically include one or more nurse call servers 92 coupled to local area network 72, one or more nurse call outlets 86 (FIG. 3) positioned in each patient room, wiring coupling the nurse call outlets 86 to nurse call server 92, and other structures. In some embodiments, nurse-call interface 52 is a wired interface adapted to couple to, and communicate with, nurse call outlet 86 via a nurse call cable 56 (FIG. 3). A first end of cable 56 is coupled to nurse-call interface 52 and the other end is coupled to nurse-call outlet 86. One example of such a wired nurse-call interface is the cable interface disclosed in more detail in commonly assigned U.S. patent application Ser. No. 15/945,437 filed Apr. 4, 2018, by inventors Krishna Bhimavarapu et al. and entitled PATIENT SUPPORT APPARATUSES WITH RECONFIGURABLE COMMUNICATION, the complete disclosure of which is incorporated herein by reference.

In other embodiments, nurse-call interface 52 is a wireless interface adapted to communicate wirelessly with nurse-call outlet 86. Several examples of wireless nurse-call interfaces 52 that enable wireless communication between patient support apparatus 20 and an adjacent nurse-call outlet 86 are disclosed in the following commonly assigned patent references and may be implemented in patient support apparatus 20 herein: U.S. patent publication 2016/0038361 filed Aug. 6, 2015, by inventors Krishna S. Bhimavarapu et al. and entitled PATIENT SUPPORT APPARATUSES WITH WIRELESS HEADWALL COMMUNICATION; U.S. patent application Ser. No. 62/600,000 filed Dec. 18, 2017, by inventor Alexander J. Bodurka and entitled SMART HOSPITAL HEADWALL SYSTEM; U.S. patent application Ser. No. 62/587,867 filed Nov. 17, 2017, by inventors Alexander J. Bodurka et al. and entitled PATIENT SUPPORT APPARATUSES WITH LOCATION/MOVEMENT DETECTION; and U.S. patent application Ser. No. 62/598,787 filed Dec. 14, 2017, by inventors Alexander J. Bodurka et al. and entitled HOSPITAL HEADWALL COMMUNICATION SYSTEM, the complete disclosures of all of which are incorporated herein by reference. Still other types of wireless or wired nurse-call interfaces may, or course, be used.

A timer 74 and/or a clock 76 may also be provided on patient support apparatus 20 for measuring one or more predetermined periods of time and/or for determining the current time of day. Timer 74 is operative to measure an interval of time having a selected duration representative of a desired function, protocol, or activity, as will be discussed more below. The timer 74 and clock 76 are in communication with controller 58. In some embodiments, timer 74 measures one or more predetermined time periods that are set by a user utilizing one of the caregiver control panels 48a and/or 48c, and/or that are set by a server on network 72, such as a patient care server 70 and/or patient support apparatus server 132. In such embodiments, the server communicates the predetermined time period to controller 58 via transceiver 68. Timer 74 may also and/or alternatively be built into a microcontroller and/or microprocessor of controller 58. Timer 74 is adapted to be reset by controller 58 in response to the predetermined time period expiring and/or one or more other actions, as will be discussed in greater detail below.

FIG. 3 depicts the hardware and data structures used in one embodiment of a patient care system 106 according to the present disclosure. Patient care system 106 includes one or more patient support apparatuses 20 in communication with a local area network 72 of the healthcare facility that includes a patient care server 70. In some embodiments of patient care system 106, patient care server 70 communicates with and utilizes the data contained within other conventional servers coupled to local area network 72. In other embodiments, patient care server 70 may operate without the assistance of any of these servers. It will therefore be understood that the precise structure and contents of the healthcare facility network 72 can vary from healthcare facility to healthcare facility and that patient care system 106 can be implemented with local area networks having different architectures and/or contents than the illustrative example of FIG. 3. Further, the data structures shown in FIG. 3 depict several examples of the types of data that may be present in a given system 106, but are not intended to be either exhaustive or exclusive of the types of data structures that different embodiments of patient care system 106 may include.

As shown, healthcare facility network 72 includes a plurality of servers, including a conventional Admission, Discharge, and Tracking (ADT) server 84, a conventional nurse call system server 92, a conventional Electronic Medical Records server 102, a caregiver assignment server 112, a caregiver tracking server 122, and a patient support apparatus server 132. Healthcare facility network 72 also includes a conventional Internet Gateway 82 that couples healthcare facility network 72 to the Internet 60, thereby enabling the servers, patient support apparatuses 20, and other applications on network 72 to communicate with computers outside of the healthcare facility, such as, but not limited to, a geographically remote cloud-based server 78 (which, in at least some embodiments, is operated under the control of the manufacturer of patient support apparatuses 20 and performs some, or all, of the functions of patient care server 70). Still further, hospital facility network 72 includes a plurality of conventional wireless access points 80 and the patient care server 70.

ADT server 84 is used for managing the admission, discharge, and transfer of patients in the healthcare facility. The ADT server 84 stores patient location information, including the identity of patients and the corresponding rooms (referred to as 403A and 401B in FIG. 3) and/or bays within rooms to which the patients are assigned. More particularly, ADT server 84 includes a patient room assignment table 108 that correlates patients to rooms (and/or bays within semi-private rooms). As shown in the example of FIG. 3, table 108 includes a column identifying patients by name and a separate column identifying the room location for each of those patients. It will be understood that table 108 may take on other forms and/or include other or additional information, such as, but not limited to, assignments of specific patients to specific patient support apparatuses. ADT server 84 is in communication with the patient care server 70 and shares patient location information with server 70, as will be discussed in greater detail below.

Nurse call server 92 communicates with caregivers and, in some embodiments, forwards alerts and/or other communications to portable wireless devices carried by caregivers and/or to audio stations positioned within patient rooms. Nurse call server 92 is in communication with a plurality of nurse call outlets 86 (FIG. 3) that are installed in locations throughout the healthcare facility, typically within each room in a location adjacent to where patient support apparatus 20 normally reside. When nurse call cable 56 is coupled between patient support apparatus 20 and the nurse call outlet 86, a patient's pressing of the nurse call button 90 (FIG. 2) on a patient support apparatus 20 is communicated to nurse call sever 92, as well as the audio signals generated by the microphone 88 of the patient support apparatus 20 in response to the patient's speech. Nurse call server 92, or one or more other structures of the nurse call system, forwards these audio signals to a nurse's station, or other location, where the assigned caregiver is typically located. When the nurse speaks into a microphone at that location, the audio signals are forwarded by nurse call server 92 back to patient support apparatus 20 and converted into sound signals by speaker 96. Nurse call server 92 may include a caregiver patient assignment table 114 that identifies which caregivers have been assigned to which patients. Depending upon the particular healthcare facility and their IT infrastructure, this data may be housed on a different server and/or it may comprise different forms, such as a caregiver assignment table 114 that correlates caregivers to rooms and/or room bays, rather than to patients.

EMR server 102 stores the patients' electronic medical records. EMR server 102 is in communication with patient care server 70 via healthcare facility network 72 and stores the digital equivalent of paper patient records or charts. Electronic medical records typically contain medical information about a patient, such as the patient's treatment, medical history, prescriptions, and/or therapies, assessments, etc. FIG. 3 shows an EMR table 116 illustrating a small exemplary portion of the type of data that is typically contained with an EMR server 102. Table 116 contains the medical records for each patient the healthcare facility and includes, in at least some instances, data identifying prescribed therapies for those patient. Such prescribed therapies may include, but are not limited to, medications that are to be taken at prescribed times, therapies to be performed on the patient, procedures and/or other tasks that are to be performed on the patient at, or by, a prescribed time, and treatments that are to be performed on the patient at, or by, a prescribed time. Patient care server 70 is configured to request certain portions of the data stored in EMR table 116 from server 112, as discussed in more detail below.

Caregiver assignment server 112 is configured to manage the work assignment of caregivers to particular patients, patient support apparatuses 20, rooms or bays within the facility, and/or units or areas within the facility. The caregiver assignment server 112 may also oversee shift assignments, the performance of specific caregiver functions, manage resources within the healthcare facility and other tasks associated with the caregivers. In general, however, caregiver assignment server 112 includes a caregiver assignment table 110 (which may, of course, take on other data forms besides a table) that matches each caregiver with those rooms and/or bays to which that particular caregiver is assigned (see FIG. 3). Alternatively, or additionally, caregiver assignment table 110, or server 112, may match each caregiver with a particular patient. Still further, caregiver assignment table 110, or server 112, may also include a data field indicating the times at which the caregivers are assigned to each of their respective rooms, bays, and/or patients.

Caregiver tracking system tracking server 122 is a real time locating and tracking server configured to receive caregiver location data for monitoring the location of caregivers within the healthcare facility. In some embodiments, caregiver tracking server 122 is part of a Real Time Location System (RTLS) that keeps track of assets and people within a healthcare facility. Real time location and tracking data is transmitted to the caregiver tracking server 122 and indicates locations within the healthcare facility at which a tracked caregiver is detected. In healthcare facilities that include a caregiver tracking server 122, each caregiver may carry or wear a locating badge 124, or other type of portable device, that wirelessly communicates with the healthcare facility network 72 and/or the caregiver tracking server 122 to track the whereabouts of the caregiver. The badge 124 can include a transmitter, for example an RFID tag, that emits a signal having information unique to the caregiver. Signal receivers can be positioned in known locations (e.g., a patient room or hallway) throughout the healthcare facility to detect signals emitted by the badge 124 worn by the caregiver. Because the signal includes information that is unique to the caregiver, caregiver tracking server 122 can determine the location of the caregiver with respect to the known signal receivers by measuring the received signal strength of the badge signals at each of the respective signal receivers. Alternatively, the badges can be configured to transmit a short range signal that is only detected by a nearby signal receiver and the location of the caregiver can be assigned to the location of the nearby receiver that receives the badge signal. As yet another alternative, transmitters can be positioned in known location(s) and transmit a signal that is detected by a receiver included in the badge 124 carried by the caregiver. The badge uses signal strengths and/or the detection of short range signals to determine its location (or alternatively forwards its detected signals to another device that determines its location, such as, but not limited to, tracking server 122). Other things can be tracked as well, including patients, medical devices, and patient support apparatuses 20. Other signaling technologies might also be used, such as Wi-Fi or other wireless-signal technologies. Tracking server 122 stores the location of the items and/or people it tracks in a location table 126 and shares this information with patient care server 70, in at least some embodiments of patient care system 106. Tracking server 122 supplements the location data received from locators 134 in some embodiments, while in other embodiments is replaces the location-detection functions server by locators 134. In still other embodiments, tracking server 122 is omitted.

Patient support apparatus server 132 communicates with patient support apparatuses 20 via the healthcare access points 80 and the transceiver 68 positioned on each of the patient support apparatuses 20. In one embodiment, patient support apparatus server 132 is a server commercially offered for sale by Stryker Medical of Kalamazoo, Mich. In other embodiments, patient support apparatus server 132 is a different type of server. Patient support apparatus server 132 coordinates communications between the various patient support apparatuses 20 in a healthcare facility and any of the other applications or servers that are present on network 72. Thus, patient support apparatus server 132 receives communications from apparatuses 20 and then forwards—or makes available—information from those communications to selected entities on network 72, as appropriate.

In at least one embodiment, patient support apparatus server 132 includes a location table 130 (or other type of data structure) that contains information correlating patient support apparatuses 20 with their location. In other embodiments, table 130 is stored elsewhere on network 72 and is accessible to server 132. Regardless of where the data of table 130 resides, location table 130 includes data identifying the unique ID's of a plurality of fixed locators 134 that are positioned in known locations throughout the healthcare facility, as well as the unique ID's of each of the patient support apparatuses, as will be discussed in more detail below. The locator ID's are communicated to an adjacent patient support apparatus 20 via short range communication (e.g. infrared) and are included, along with the patient support apparatus ID, within the messages sent by the patient support apparatus 20 to the patient support apparatus server 132. Table 130 correlates the locator ID's to their location, and also keeps track of which patient support apparatuses are currently in which rooms and/or bays using the locator ID's, the known location of each of the fixed locators 134, and the patient support apparatus ID's.

In addition to the unique ID of the fixed locator 134 with which an adjacent patient support apparatus 20 is in communication, patient support apparatuses 20 are also configured to communicate additional information to patient support apparatus server 132. Such additional information includes the status of various components and/or systems onboard patient support apparatus 20, such as, but not limited to, the armed/disarmed state of exit detection system 94, the state of the brake, the state of siderails 34 (raised or lowered), the height of litter frame 28, etc.

Fixed locators 134 can be positioned on walls, ceilings, or in other fixed locations whose absolute positions within the healthcare facility are known. Further, each fixed locator 134 includes a location identifier that uniquely identifies and distinguishes that particular locator 134 from all other such locators 134 within the healthcare facility. Location transceivers 136 are incorporated into some or all of the patient support apparatuses 20. In the example of FIG. 3, location transceiver 136 feeds the unique location ID it receives from an adjacent fixed locator 134 to controller 58 which appends it, or otherwise incorporates it into, messages transmitted to patient support apparatus server 132 and/or to patient care server 70.

In one embodiment, a healthcare facility may have a plurality of patient support apparatuses 20 that are beds that include such transceivers 136, while other types of patient support apparatuses 20—such as stretchers, cots, and the like—might not include such locator transceivers 136. Regardless of which specific patient support apparatuses 20 have location transceivers 136 incorporated therein, any such apparatus 20 having a location transceiver 136 incorporated therein will be able to communicate with a fixed locator 134 when the apparatus is within a relatively close proximity thereto. Such proximity may be on the order of five to ten feet, or it may be other distances. In some embodiments, location transceiver 136 communicates with fixed locators 134 via infrared signals, although it will be understood by those skilled in the art that other types of signals may be used for communication between locators 134 and transceiver 136. Fixed locator 134 sends a location identifier that uniquely identifies the fixed locator 134 to the location transceiver 136 when the patient support apparatus 20 is positioned sufficiently adjacent the fixed locator 134.

In general, because the locations of locators 134 are known, and because the patient support apparatuses can only communicate with a given locator 134 (via transceivers 136) when they are within a close proximity to the given locator 134, the very establishment of such communication indicates that the patient support apparatus 20 is in close proximity to a given locator 134 whose location is known. This allows the location of a patient support apparatus 20 to be determined. Further details of the operation of locators 134 and transceivers 136, as well as the manner in which they can be used to determine location, are found in commonly assigned, U.S. patent application Ser. No. 12/573,545 filed Oct. 5, 2009 by applicants David Becker et al. and entitled LOCATION DETECTION SYSTEM FOR A PATIENT HANDLING DEVICE and U.S. patent application Ser. No. 15/909,131 filed Mar. 1, 2018 by applicants Michael Joseph Hayes et al. and entitled PATIENT SUPPORT APARATUS COMMUNICATION SYSTEMS, the complete disclosures of which are also incorporated by reference herein. Fixed locators 134 may also take on any of the forms, and perform any of the functions, disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION; Ser. No. 16/217,203 filed Dec. 12, 2018, by inventor Alex Bodurka, and entitled SMART HOSPITAL HEADWALL SYSTEM; Ser. No. 16/193,150 filed Nov. 16, 2018, by inventors Alexander Bodurka et al. and entitled PATIENT SUPPORT APPARATUSES WITH LOCATION/MOVEMENT DETECTION; and Ser. No. 16/215,911 filed Dec. 11, 2018, by inventors Alex Bodurka et al. and entitled HOSPITAL HEADWALL COMMUNICATION SYSTEM, the complete disclosures of all of which are incorporated herein by reference.

As was noted previously, the particular servers on network 72 may vary from healthcare facility to healthcare facility. In addition to any of the servers previously discussed, network 72 may further include a conventional mobile communications server, a conventional work flow server and/or a charting server. Such servers are configured to assign, monitor, and/or schedule patient-related tasks to particular caregivers, and/or to forward communications to particular individuals within the healthcare facility, such as via one or more portable devices (smart phones, pagers, beepers, laptops, etc.). The forwarded communications may include data and/or alerts that originate from patient support apparatuses 20. In some embodiments, the communications are forwarded via WiFi to one or more of cell phones, pagers, personal digital assistants (PDAs), laptop computers, and/or to electronic devices with WiFi communication abilities. Any information that is transmitted to network 72 via transceiver 68 of patient support apparatus 20, or by network transceivers incorporated into other devices, can therefore cause an alert to be forwarded to the appropriate caregiver(s), depending upon the contents of such information.

Patient care server 70 receives information from patient support apparatuses 20 and, in some embodiments, sends messages and/or data back to patient support apparatuses 20. Patient care server 70 also communicates with one or more of the other servers that are coupled to network 72, as will be discussed in greater detail below. As will also be discussed in greater detail below, at least one of the messages that patient care server 70 is configured to send to one or more servers and/or other devices in communication with network 72 is an inactivity alert. The inactivity alert indicates that a particular patient support apparatus 20 has not had any caregiver activity associated with it for a certain time period, and it may behoove the healthcare personnel to check on that particular patient support apparatus 20 to ensure that the patient associated with that patient support apparatus 20 is properly being cared for. Patient care server 70 may further be configured to share data with other servers 84, 92, 102, 122, and 132 on the network 72 and/or with other servers located geographically remote from the healthcare facility (via Internet 60).

Figure 4:
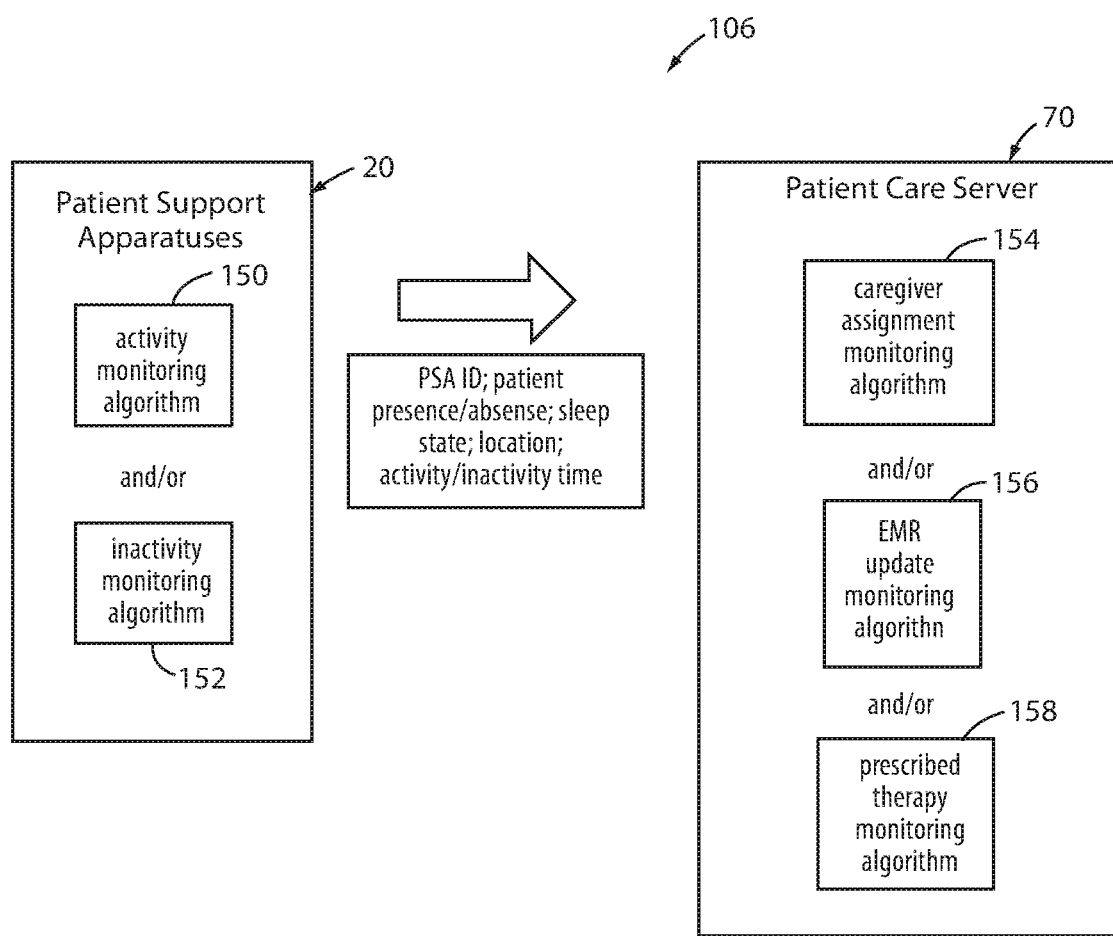
FIG. 4 is a diagram of various software algorithms used in at least one embodiment of the patient care system of the present disclosure.

FIG. 4 illustrates a set of algorithms carried out by one embodiment of a patient care system 106 according to the present disclosure. As noted, patient care system 106 includes one or more patient support apparatuses 20 and patient care server 70, and the algorithms utilized by patient care system 106 may be executed solely on patient support apparatuses 20, solely on patient care server 70, or a combination of both patient support apparatuses 20 and server 70. Patient care system 106 functions to help ensure that no patients within a healthcare facility are neglected, not visited by healthcare personnel, and/or don't have prescribed treatment delayed for longer than a threshold amount of time. Patient care system 106 accomplishes this function through communications between patient care server 70 and patient support apparatuses 20, as well as through communications with one or more of the other servers on network 72, as will be discussed in greater detail below.

FIG. 4 illustrates a patient care system 106 in which the patient support apparatuses 20 execute two algorithms: an activity monitoring algorithm 150 and an inactivity monitoring algorithm 152. In practice, each patient support apparatus 20 will typically only execute one of these two algorithms 150, 152, rather than both algorithms. In a particular embodiment of patient care system 106, however, a first set of patient support apparatuses 20 might execute one of algorithms 150, 152, while a second set of patient support apparatuses 20 might execute the other one of algorithms 150, 152.

Patient care server 70 is shown in FIG. 4 to execute a plurality of algorithms, including a caregiver assignment monitoring algorithm 154, an EMR update monitoring algorithm 156, and a prescribed therapy monitoring algorithm 158. In some embodiments of patient care system, patient care server 70 executes all three of these algorithms 154, 156, and 158, while in other embodiments, patient care server 70 executes only one or two of these algorithms. Still further, in some embodiments of patient care system 106, patient care server 70 executes one or more other algorithms different from those shown in FIG. 4, several examples of which will be discussed in greater detail herein. It will be understood that, in some embodiments of patient care system 106, patient support apparatuses 20 execute one or more of algorithms 150 and 152 while patient care server executes none of algorithms 154, 156, or 158; while in other embodiments of patient care system 106, patient support apparatuses 20 execute neither of algorithms 150 or 152, while patient care server 70 executes one or more of algorithms 154, 156, and/or 156. In other words, patient care system 106 may include any combination or permutation of the various algorithms shown in FIG. 4 in a particular embodiment, as well as combinations and/or permutations of other algorithms discussed herein. In some embodiments of system 106, an authorized administrator of the healthcare facility can access patient care server 70 via a computer with access to local area network 72 (e.g. computer 120; FIG. 3) and select which ones of algorithms 150-158 he or she would like have executed. This customization of patient care system 106 can also extend to modifying the selected algorithms, including setting various threshold, configuring the communication preferences of alerts, and other items, as will be discussed in greater detail below.

In carrying out algorithms 150-158, patient support apparatuses 20 transmit a set of data 128 to patient care server 70, either directly or indirectly, that is utilized by patient care server 70 in the performance of its functions. In the example shown in FIG. 4, the data set 128 includes the unique ID of the patient support apparatus 20 (PSA ID); an indication of whether or not the patient is currently occupying the patient support apparatus 20; an indication of whether or not the patient is asleep or awake; location information that either identifies the location of patient support apparatus 20 directly, or provides sufficient information for patient care server 70 to determine the location of the patient support apparatus 20 within the healthcare facility; and inactivity or activity data indicating either the presence or lack of caregiver interaction with the patient and/or his or her patient support apparatus 20.

Although FIG. 4 illustrates data set 128 as a single data set, it will be understood that data set 128 may be transmitted in one or more separate messages to patient care server, and that the frequency of those individual messages may vary, depending upon the content of the messages. For example, the patient support apparatus 20 may only send its location information whenever the location of the patient support apparatus 20 changes, while it may send activity/inactivity status data at regular intervals and/or at a greater frequency than the location data. It will also be understood that the data of data set 128 may be communicated to patient care server 70 in a variety of different manners. For example, in some embodiments, patient support apparatus 20 may send certain data of data set 128 directly to the IP address of patient care server 70. Other data contained within data set 128 may be first sent to another server on network 72 before being passed on, either with or without additional processing, to patient care server 70. For example, in some embodiments, patient support apparatuses 20 are configured to send their location data directly to patient support apparatus server 132, and patient care server 70 retrieves this location from patient support apparatus server 132, rather than individually from each of the patient support apparatuses 20. It will further be understood that, although FIG. 3 illustrates patient care server 70 as separate from the other servers shown therein, patient care system 106 can be modified in some embodiments such that its functionality is combined with other servers, such as, but not limited to, patient support apparatus server 132. It will also be understood that the term server, as used herein (unless otherwise stated) is being used to refer to a software server, not a hardware server. Accordingly, any one or more of the servers shown in FIG. 3 may be executed on the same physical machine, or they may be executed on different physical machines.

The data shown in data set 128 of FIG. 4 is only one example of the type of data that patient support apparatuses 20 may provide to patient care server 70. Additions, substitutions, and/or omissions from this set of data may be made in different embodiments of patient care system 106. As one example, in some embodiments, patient support apparatuses 20 do not include sensors to detect whether the patient is asleep or not and therefore do not send data indicating whether the patient is awake or asleep to patient care server 70. In other embodiments, if patient support apparatuses 20 are not executing the activity or inactivity monitoring algorithms 150, 152, the data indicating caregiver activity and/or inactivity is omitted from data set 128, and the data indicating whether the patient is present or absent on patient support apparatus 20 may also be omitted. Still other variations are possible.

Figure 5:
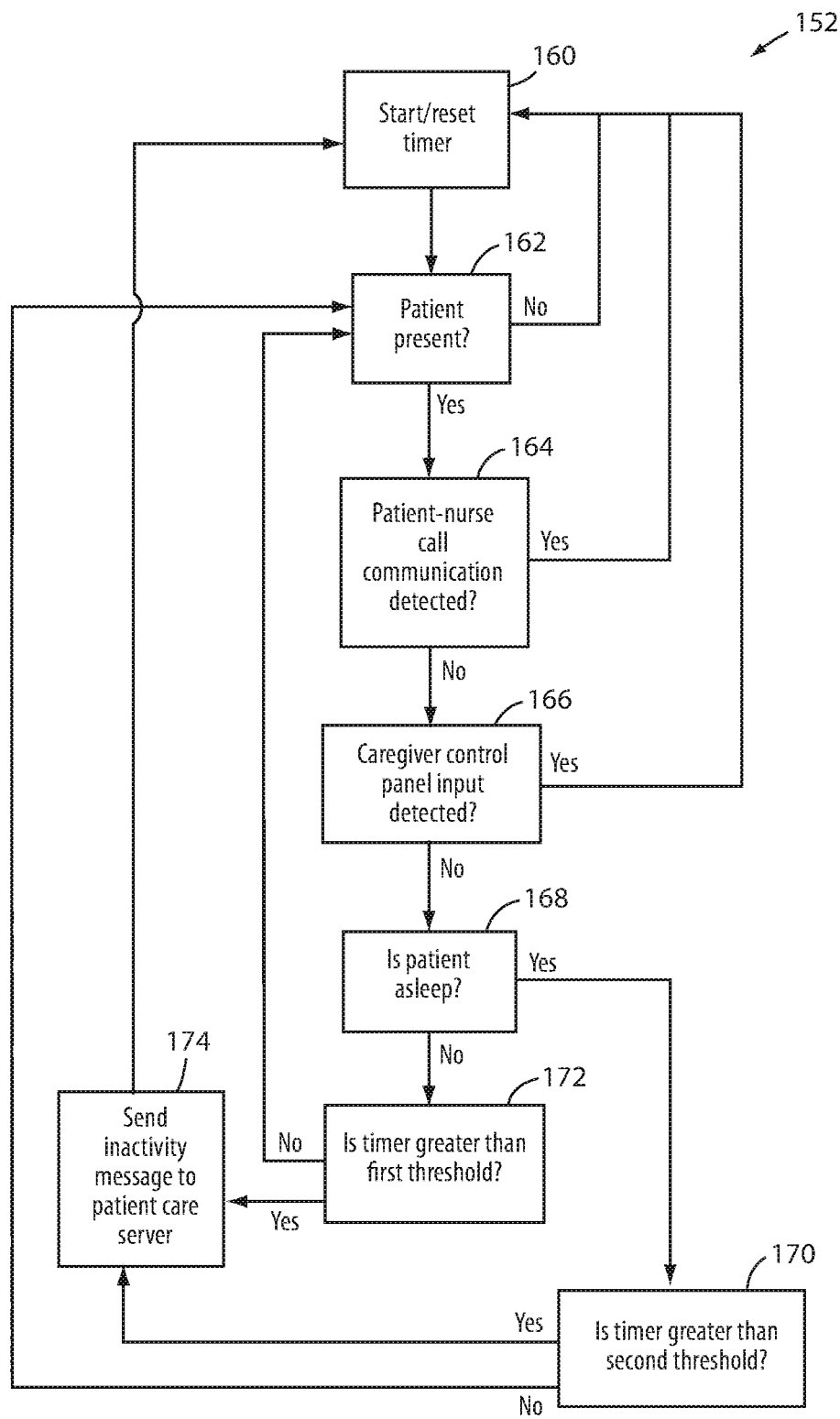
FIG. 5 is a flow chart of the caregiver inactivity algorithm of FIG. 4 executed by the patient support apparatus of FIG. 1.

FIG. 5 illustrates one embodiment of inactivity monitoring algorithm 152. Inactivity monitoring algorithm 152 is executed by controller 58 of each patient support apparatus 20, either wholly or partially (e.g. in some embodiments, one or more other controllers on board patient support apparatus 20—e.g. scale/exit detection system controller 98—may execute, or assist in, the execution of one or more steps of algorithm 152). Algorithm 152 begins at a step 160 where controller 58 initiates, or resets, timer 74. In some embodiments, algorithm 152 is automatically and repetitively executed whenever patient support apparatus 20 is turned on. In other embodiments, algorithm 152 is initiated in response to a message receiver from patient care server 70, or another authorized device (e.g. mobile electronic device 138) that is in communication with local area network 72. Still other manners of starting algorithm 152 may be implemented.

After starting timer 74 at step 160 (FIG. 5), controller 58 proceeds to step 162 where it determines whether or not a patient is present on patient support apparatus 20. Controller executes step 162 in conjunction with one or more of the patient presence sensors 62 discussed previously. That is, controller 58 analyzes the outputs from the one or more patient presence sensors 62 positioned onboard patient support apparatus 20 and determines if the patient is currently occupying the patient support apparatus 20 or not. If there is no patient present, controller 58 returns to start step 160 and resets the timer. If a patient is present, controller 58 proceeds to step 164 where it determines if a nurse call communication is taking place (or has taken place since the previous time step 164 was performed).

Controller 58 determines if a nurse call communication has taken, or is taking, place by monitoring the particular pin and/or wire within nurse call interface 52 that carries the audio signal from remotely positioned nurse. That is, when a patient places a nurse call by activating nurse call button 90, a signal is sent through nurse call interface 52 on a specific wire or pin that, via the connection of cable 56 to nurse call outlet 86, notifies the nurse call system the patient has placed a call. If a remotely positioned nurse answers the call and talks back to the patient, his or her audio signals are transmitted back to nurse call interface 52, and communicated to a specific audio pin or wire within nurse call interface 52. Controller 58 forwards these audio signals to speaker 96 for playback. Controller 58 also monitors these signals to determine if a nurse call communication is taking place, or has taken place since the last time step 164 was performed. In the latter case, controller 58 is configured to constantly monitor when audio signals are received from a remote nurse and to flag such occurrences including, in some embodiments, a time when the communication took place and/or the amount of time that has elapsed since such occurrences. This flag is stored in memory onboard patient support apparatus 20 and retrieved by controller 58 during the performance of step 164.

If a nurse call communication is determined to be taking place, or have taken place, at step 164, controller 58 returns to step 160 and resets the timer. This return to step 160 occurs because it is presumed that if a patient is talking to a remote nurse, or has recently talked to a remote nurse, he or she is not being neglected. In some embodiments, controller 58 and algorithm 152 may be modified to monitor other aspects of the nurse call rather than the audio pin (or wire) that delivers audio signals from the remotely positioned nurse to speaker 96. For example, in some embodiments, controller 58 may monitor the pressing of the nurse call button 90. The mere pressing of the nurse call button 90, however, is less preferred because it does not exclude the possibility that a nurse did not answer the nurse call button 90, and therefore does not exclude the possibility that the patient is being neglected.

If controller 58 determines at step 164 that no such communication is taking, or has taken, place, controller 58 proceeds to step 166. At step 166, controller 58 determines if any of the caregiver controls on patient support apparatus 20 are being pressed, or otherwise activated, or if they have been pressed or otherwise activated since the last time step 166 was executed. The caregiver controls refer to those controls that are positioned on either footboard control panel 48a or either of the outside control panels 48c. Each time one of those controls is activated, controller 58 is informed of the activation and records (at least temporarily) the activation. At step 166, controller 58 determines if any of those activations have occurred since the last time step 166 was executed (or, in some embodiments, at any time within a predetermined time window). It should be noted that controls that are positioned on patient control panels 48b are not considered during step 166. This is because these control panels are presumed to be activated by the patient, and are therefore not indicative of a caregiver being present at the patient support apparatus. Control panels 48a and 48c, on the other hand, are presumed to be controls that are not activated by the patient, and therefore can be used as an indicator of caregiver presence or absence.

Step 166 may be modified and/or supplemented in a number of different manners. Step 166 is performed essentially to determine if a caregiver is present adjacent patient support apparatus 20, and such a determination can be made in a variety of different manners. For example, in some embodiments, rather than detecting if a caregiver activates any controls on control panels 48a or 48c, patient support apparatus 20 is constructed to include one or more caregiver presence detectors 144 that positively detect the presence or absence of a nearby caregiver. As was described previously, caregiver presence detectors 144 are adapted to detect the presence of a caregiver within the vicinity of patient support apparatus 20. If a caregiver is detected at step 166 (whether through caregiver presence sensors 144 or via the activation of a control on the caregiver control panel 48a or 48c, or a combination thereof), controller 58 returns back to step 160 and re-starts timer 74. If a caregiver is not detected at step 166, controller 58 proceeds to step 168.

At step 168, controller 58 determines if the patient is currently sleeping or not. As will be described more below, controller 58 uses this determination in some embodiments to select different time thresholds that constitute neglect. That is, when a patient is sleeping, patient care system 106 is configured in some embodiments to allow longer periods of time to elapse without a caregiver visit before issuing an alert. This may allow the patient to sleep longer without interruption and/or allow the caregivers to take care of other duties without needlessly checking in on the patient and/or awaking the patient. Of course it will be understood that this feature may be omitted in some embodiments, and patient support apparatuses 20 may be incorporated into patient care system 106 that do not include any sleep detection sensors.

In those embodiments of patient care system 106 that include a sleep detection sensor 142 built into the patient support apparatuses 20, such sleep detection sensors 142 may take on a variety of different forms. In some embodiments, controller 58 utilizes the outputs from load cells 54 to determine, either alone or in concert with other data, whether the patient is awake or asleep. When using load cells 54 to determine the sleep state of the patient, the outputs of the load cells may be analyzed to detect one or more vital signs of the patient, such as, but not limited to, the patient's heart rate and/or respiration rate. One method of utilizing load cells to detect a patient's heart rate and/or breathing rate using load cells is disclosed in commonly assigned U.S. Pat. No. 7,699,784 issued to Wan Fong et al. and entitled SYSTEM FOR DETECTING AND MONITORING VITAL SIGNS, the complete disclosure of which is incorporated herein by reference.

Sleep sensors 142 may take on a variety of other forms. In one embodiment of patient support apparatuses 20, sleep sensors 142 take on any one or more of the forms of sleep sensors disclosed in commonly assigned U.S. patent publication 2016/0022218 published Jan. 28, 2016, and filed by inventors Michael Hayes et al. and entitled PATIENT SUPPORT APPARATUS WITH PATIENT INFORMATION SENSORS, the complete disclosure of which is incorporated herein by reference. Still other types of sleep sensors 142 may be utilized.

If controller 58 determines at step 168 that the patient is asleep, controller 58 proceeds to step 170. If controller 58 determines at step 168 that the patient is awake, controller 58 proceeds to step 172. At step 172, controller 58 determines if the amount of time that has elapsed since timer 74 was started (and not reset) is greater than a first threshold. The particular value of the first threshold can vary widely, and as noted previously, may be customized by an authorized administrator of the healthcare facility using computer 120. In some embodiments, the value of the first threshold may be in the range of approximately two hours. Other ranges can, of course, be utilized depending upon how frequently the administrators of the healthcare facility wish to ensure patient-caregiver interactions. If the amount of time that has passed, as measured by timer 74, is determined at step 172 to be greater than the first threshold (which is a threshold used when the patient is awake), controller 58 proceeds to step 174 and issues an inactivity alert. After issuing an inactivity alert at step 174, controller 58 returns to step 160, resets the timer, and restarts algorithm 152 (FIG. 5).

When controller 58 issues an inactivity alert, it sends a message to patient care server 70 (and/or patient support apparatus server 132) that is then forwarded to appropriate personnel within the healthcare facility. The particular individual(s) who receive such an alert may be customized and configured by healthcare personnel using computer 120, or some other electronic device having authorized access to network 72. In some embodiments, server 70 (or server 132) sends a message directly to a mobile electronic device 138 (FIG. 3) carried by the caregiver or caregivers who are assigned to the patient in the patient support apparatus 20 whose controller 58 sent the alert. The mobile electronic device 138 may be a smart phone, a tablet, a laptop, a badge, or some other type of mobile electronic device. The alert message may be an email, a text message, a phone call, or the like.

Patient care server 70 determines the correct recipients of the alert message in one or several manners. In a first embodiment, patient care server 70 uses the location of the patient support apparatus 20 that sent the alert message to determine which caregiver is assigned to the patient who is assigned to that particular patient support apparatus 20. This is accomplished by sending a query to another server that maintains a correlation between room locations (and/or bay locations) and caregivers, such as, but not limited to, caregiver assignment server 112. As noted previously, caregiver assignment server 112 includes a table 110 that correlates assigned caregivers to room locations. Using this information, patient care server 70 determines who the caregiver(s) is/are who should receive the inactivity message generated at step 174. Patient care server 70 has access to a memory in which the phone number, email address, and/or other contact information is stored for each of the caregivers within the facility. This contact information may be input by an authorized administrator during the setup of patient care system 106, or it may be obtained by patient care server 70 sending one or more queries to other servers within the healthcare facility that contain this contact information.

In another embodiment, patient care server 70 does not sent out an inactivity alert message directly to any caregivers or other personnel, but instead sends a message to one or more communications servers on network 72 that send out the message to the intended recipient. In still other embodiments, other manners of sending out the inactivity alert message may be utilized.

If controller 58 determines at step 168 of algorithm 152 (FIG. 5) that the patient is asleep, it proceeds to step 170, as noted. At step 170, controller 58 makes the same determination it does at step 172, but uses a different time threshold. As noted, controller 58 uses a larger time threshold at step 170 than it does at step 172. This larger time threshold is chosen because it is presumed that it is acceptable to have less frequent patient-caregiver interactions when the patient is asleep than when the patient is awake. If this assumption is not true or desirable for a given healthcare facility, patient care system 106 and patient care server 70 can be modified to execute an algorithm 152 that utilizes only a single threshold (i.e. algorithm 152 is modified to remove steps 168 and 170, and controller 58 instead proceeds from step 166 directly to step 172.)

In those embodiments of algorithm 152 that include step 168 and step 170, controller 58 proceeds to step 174 if the timer has a value greater than the second threshold, as determined at step 170. At step 174, as described previously, controller 58 issue an inactivity alert and sends a message to patient care server 70 and/or patient support apparatus server 132. If controller 58 determines at step 170 that the timer 74 has a value that is less than the second threshold, it returns to step 162 and proceeds in the manner previously described. Algorithm 152 therefore causes controller 58 to issue an alert if none of the caregiver controls on patient support apparatus 20 are activated within a given time period (e.g. a first or second threshold, depending on the patient's sleep state) and the caregiver has not communicated with the patient via the nurse call system and speaker 96 within that given time period. Although it is possible that a caregiver may have visited the patient in person and simply not pressed any buttons on the patient support apparatus 20, this is not typical. Further, in order to avoid incorrect inactivity alerts due to this type of caregiver-patient visit, patient support apparatus 20 and algorithm 152 can be modified to detect such visits (with no patient support apparatus 20 interaction), as will be discussed in greater detail below with respect to caregiver detection sensors 144 and the inactivity algorithm of FIG. 10.

It will be understood that a variety of modifications can be made to algorithm 152. These include, but are not limited to, changing the order of any of the steps of algorithm 152. These also include omitting the determination of whether the patient is asleep or not, omitting the determination of patient presence, and/or omitting the use of multiple thresholds. Such modifications also include adding one or more additional steps, such as, but not limited to, detecting the presence of a caregiver adjacent the patient support apparatus 20 using one or more caregiver presence sensors 114, as noted previously. Still further, in some embodiments, one or both of the thresholds may be dynamic and change value depending upon the time of day, the location of the patient support apparatus 20 within the healthcare facility (e.g. different wards or wings have different values), and/or other factors. With respect to the time of day, for example, if clock 76 indicates that the time of day is within "daytime" hours (e.g. 8 am-10 pm), the first or second threshold might be set to a normal period of time (e.g. two to three hours). In contrast, if clock 76 indicates that the time of day is within "nighttime" hours (e.g. 10 pm-8 am), the first or second threshold might be extended to a longer period of time (e.g. 4-6 hours). Still other modifications are possible.

Figure 6:
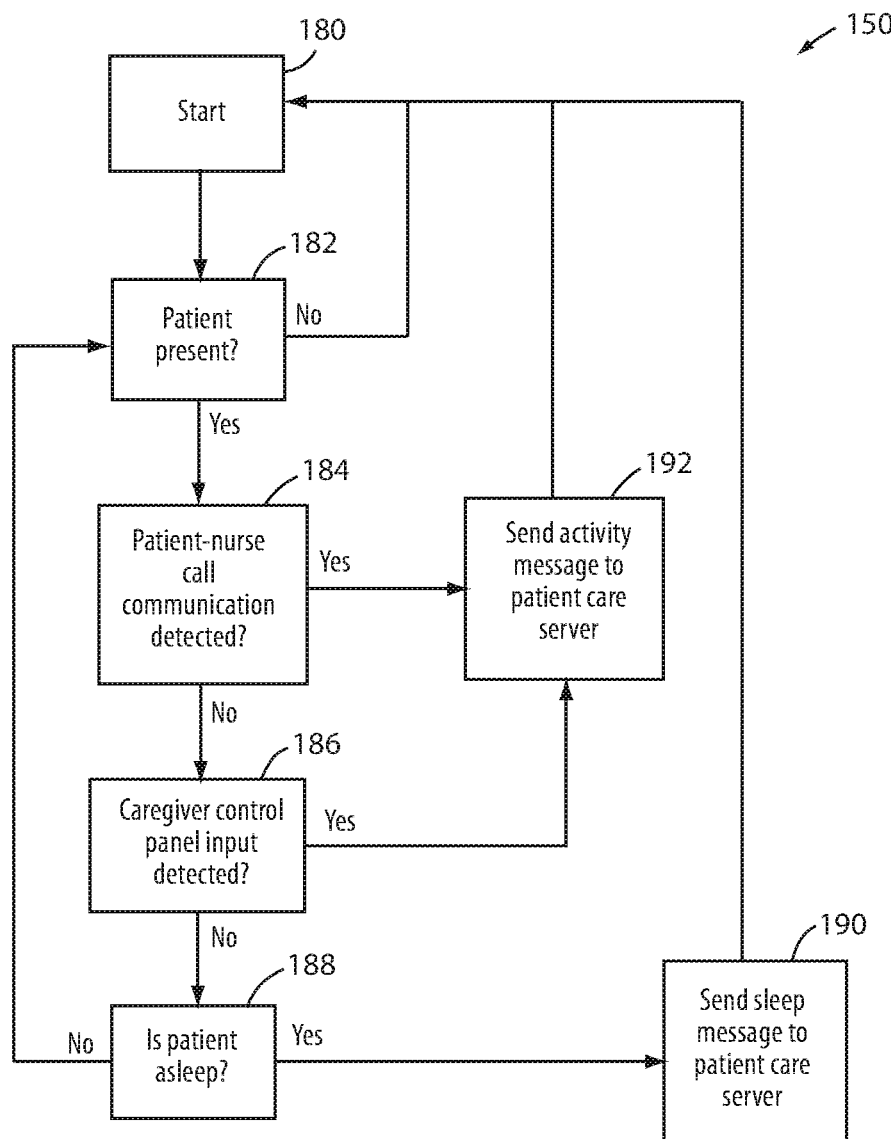
FIG. 6 is a flow chart of the caregiver activity algorithm of FIG. 4 executed by the patient support apparatus of FIG. 1.

FIG. 6 illustrates a caregiver activity monitoring algorithm 150 according to one embodiment of the present disclosure. Caregiver activity monitoring algorithm 150 is, in a general sense, the opposite of caregiver inactivity monitoring algorithm 152. That is, instead of sending out a message when caregiver inactivity is detected for more than a threshold amount of time (as with inactivity monitoring algorithm 152), algorithm 150 sends out activity messages whenever caregiver activity is detected. Patient care server 70 is modified in this embodiment to process the received activity messages from each of the patient support apparatuses 20 and to note if no such messages are received from a patient support apparatus 20 for more than a threshold amount. Thus, in general, caregiver activity monitoring algorithm 150 offloads from the patient support apparatuses 20 to patient care server 70 some of the timing and threshold comparison calculations that are performed in algorithm 152, as will become clear from the following detailed description of activity monitoring algorithm 150.

Activity monitoring algorithm 150 (FIG. 6) begins at step 180. Step 180 may be triggered in the same manner as step 160 of algorithm 152. That is, in some embodiments, step 180 commences automatically in response to power being turned on to the patient support apparatus, or in response to any of the other triggering events discussed above with respect to step 160. Once started, controller 58 proceeds to step 182 and determines if a patient is currently present on the patient support apparatus 20. This is performed in the same manner as step 162 of algorithm 152 and need not be described further. If no patient is present, controller 58 returns to start step 180. If a patient is present, controller 58 proceeds from step 182 to step 184. At step 184, controller 58 determines if a patient-nurse call communication has taken place, or is currently taken place. This is performed in the same manner as step 164 of algorithm 152 and need not be described further. If such a communication is taking place, or has taken place since the last iteration of algorithm 150, controller 58 proceeds to step 192. At step 192, controller 58 sends an activity message to patient care server 70 using transceiver 68 (which sends the message to patient care server 70 via one or more wireless access points 80 and network 72).

Patient care server 70 receives the activity message from patient support apparatus 20 and notes the time at which the message was received. The receipt of such a message resets a timer maintained at patient care server 70. Such a timer is maintained for each patient support apparatus 20 in which patient care server 70 is in communication (and configured with patient care system 106). Whenever an activity message is received from one of these patient support apparatuses 20, patient care server 70 resets the timer for the particular patient support apparatus 20 from which the activity message was received. In addition to resetting the timers in response to such activity messages, patient care server 70 is configured to monitor the timers and issue an alert for any of the timers that reach more than a first or second threshold. The first and second thresholds, in one embodiment, are the same as the first and second thresholds used in steps 172 and 170 of algorithm 152, and the choice of which threshold to utilize is based on the sleep state of the patient. Alternatively, patient care server 70 may be configured to use only a single threshold regardless of whether the patient is awake or asleep. As will be discussed more below, when using multiple thresholds, patient care server 70 is apprised of the sleep status of the patient at another step in algorithm 150 (i.e. step 190, discussed below).

For any one or more of the timers maintained at patient care server 70 that exceed the corresponding threshold, patient care server 70 issues an inactivity alert for those particular patient support apparatuses 20. The inactivity alert is processed in the same manner discussed above with respect to algorithm 152. That is, patient care server 70 sends out a message to one or more caregivers associated with the patient support apparatus 20 that hasn't reported an activity message for longer than the corresponding threshold period of time. The message may be sent to the mobile electronic device(s) 138 associated with the caregiver(s) for that particular patient. The message may be a text, email, voice message, or some other type of message.

Returning back to step 184 of algorithm 150 (FIG. 6), if controller 58 does not detect any patient-nurse communications at step 184, it moves to step 186. At step 186, controller 58 determines if any caregiver control has been activated since the last iteration of step 186. Step 186 is the same as step 166 of algorithm 152 and refers to the same caregiver controls (e.g. those on caregiver control panels 48a and 48c, but not patient control panels 48b). If the use of a caregiver control is detected at step 186, controller 58 proceeds to step 192 where it sends out an activity message to patient care server 70, as described above. If no caregiver control activity is detected at step 186, controller 58 proceeds to step 188 where it determines if the patient is asleep or awake. This is performed in the same manner as step 168 of algorithm 152. If the patient is not asleep, controller 58 returns to step 182 and proceeds in the manner previously discussed. If the patient is asleep, controller 58 proceeds to step 190 where it sends a sleep message to patient care server 70 informing the server 70 that the patient is currently asleep. As was noted, patient care server 70 uses this message, in at least some embodiments, to determine which threshold time period to utilize before sending out an inactivity alert to the corresponding caregivers. If patient care server 70 utilizes only a single time threshold, step 190 may be omitted from algorithm 150.

It will be understood that algorithm 150 may be modified in many of the same manners as algorithm 152 discussed above. These include, but are not limited to, changing the order of the steps, adding additional steps and/or omitting one or more of the additional steps and/or modifying any one or more of these steps. In one embodiment, in order to reduce the bandwidth that might otherwise be consumed by patient support apparatuses 20 when a caregiver presses multiple buttons on one of the caregiver controls panels 48a and/or 48c, algorithm 150 may be modified consolidate the activity messages that are sent at step 192. Thus, for example, instead of sending out an activity message every time a caregiver control panel is activated, or every time patient-nurse call communication is detected, controller 58 can be configured to only send out one activity message per given time period of caregiver activity detection (e.g. one message every five minutes, ten minutes, an hour, etc.) Thus, for example, instead of sending ten activity messages out if the caregiver presses ten buttons within a short time period, controller 58 may be configured to send only one message out in response to the initial button press (or other caregiver control activation) and then send no more activity messages out unless another button press (or other caregiver control activation) is detected five minutes later (or whatever the selected time period is). Still other modifications are of course possible.

For either of algorithms 150 and 152, the threshold time periods (e.g. those used at steps 170, 172 of algorithm 152 or by patient care server 70 in algorithm 150) are set by the manufacturer of the patient support apparatus 20 and stored in the memory of patient support apparatus 20, in at least one embodiment. In such embodiments, these time thresholds can be overridden by authorized healthcare personnel, either by using one of the caregiver control panels 48*a*, 48*c*, or by sending a message to patient support apparatus 20, such as via computer 120 or through other means. In other embodiments, the patient support apparatuses 20 include no time threshold(s) initially, and must have such threshold(s) input by an authorized person of the healthcare facility or other authorized individual. In any of these embodiments, as was noted previously, the time threshold(s) can be modified by authorized personnel and/or can be dynamic and take into account such factors as time of day, location within the healthcare facility, diagnosis of the patient, etc.

Figure 7:
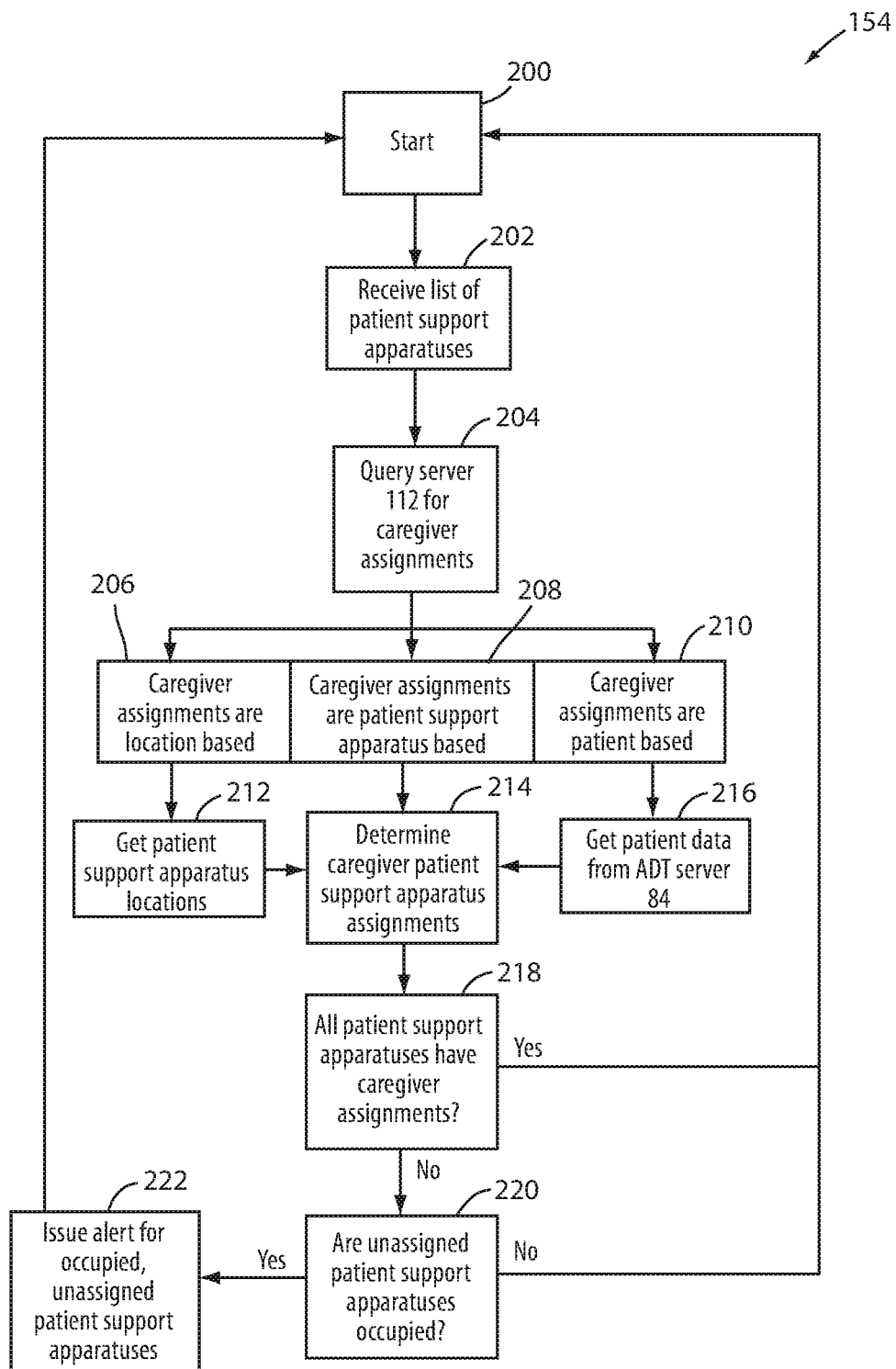
FIG. 7 is a flowchart of the caregiver assignment monitoring algorithm of FIG. 4 executed by the patient care server of FIG. 3.

FIG. 7 illustrates one embodiment of a caregiver assignment monitoring algorithm 154 according to the present disclosure. Caregiver assignment algorithm 154 is executed by patient care server 70 and involves communications with both patient support apparatuses 20 and one or more other servers on network 72. Caregiver assignment algorithm 154 begins at a step 200. In some embodiments, algorithm 154 begins automatically every time patient care server 70 is powered up. In other embodiments, algorithm 154 runs automatically in response to a passage of a predetermined time interval, while in still other embodiments, algorithm 154 runs in response to a message from an authorized user. In still other embodiments, algorithm 154 may be configured to begin in response to a combination of two or more of these factors.

After beginning at step 200, patient care server 70 proceeds to step 202 where it receives a list of all of the patient support apparatuses 20 that are located within the healthcare facility and that are desirably monitored. In some embodiments, this list is input into patient care server 70 manually by an authorized individual, and in some such embodiments, it includes all of the patient support apparatuses 20 that the healthcare facility has purchased and obtained. In other embodiments, the list may be a subset of the entire set of patient support apparatuses 20 within the healthcare facility. Still further, in some embodiments, patient care server 70 automatically generates the list of all patient support apparatuses 20 by tallying the list of patient support apparatuses 20 with which it is able to communicate. This may be done by sending messages to all of the patient support apparatuses 20, or it may be done by querying patient support apparatus server 132, which may itself contain a list of all of the patient support apparatuses 20 within the healthcare facility. Still other variations are possible.

After obtaining the list of patient support apparatuses 20 at step 202, patient care server 70 proceeds to step 204 of algorithm 154 (FIG. 7). At step 204, patient care server 70 is programmed to send a query to whichever server (or servers) on network 72 contains a list of caregiver assignments. The particular server that contains this information is identified to patient care server 70 during installation of patient care system 106 (and/or modified after installation, as appropriate) such that patient care server 70 stores the data necessary to communicate with that particular server (e.g. IP address, authentication credentials, etc.). Depending upon the particular healthcare facility, this information may be stored in at least three different manners. First, a particular healthcare facility may assign caregivers to specific patients. Second, a particular healthcare facility may assign caregivers to specific locations (e.g. rooms and/or bed bays within a room). And third, a particular healthcare facility may assign caregivers to specific patient support apparatuses 20. Patient care system 106 and server 70 are configured to accommodate any of these three scenarios, and follow one of paths 206, 208, and 210 depending upon how a particular healthcare facility has chosen to assign caregiver responsibilities.

Patient care server 70 follows path 206 if the healthcare facility assigns caregivers to locations (rooms, bed bays, etc.), and therefore proceeds to step 212 after completing step 204. If the healthcare facility assigns caregivers to patient support apparatuses 20, then server 70 follows path 208 and proceeds to step 214 after completing step 204. Finally, if the healthcare facility assigns caregivers to individual patients, then server 70 follows path 210 and proceeds to step 216 after step 204. These three different paths are discussed more below.

If patient care server 70 follows path 206, then the healthcare facility has chosen to assign caregivers to rooms and/or bed bays within rooms and patient care server 70 determines the locations of the patient support apparatuses 20 at step 212 (FIG. 7). In some embodiments, patient care server 70 determines the list of patient support apparatus locations at step 212 by sending a query to patient support apparatus server 132 for this list. In other embodiments, patient care server 70 generates the list by sending out a request to each patient support apparatus asking it to send it its location information. Still other methods of determining the locations of the patient support apparatuses are possible. After getting the list of patient support apparatus locations at step 212, patient care server 70 proceeds to step 218 where it determines which caregivers has been assigned to which patient support apparatuses 20. This is accomplished by sending an inquiry to whatever server contains the list of caregiver-location assignments. In the example shown in FIG. 3, caregiver assignment server 112 contains this list (table 110), so patient care server 70 sends an inquiry to server 112 asking it for the list of caregiver-room assignments. Once this list is obtained, patient care server 70 proceeds to step 218, which will be discussed further below.

If patient care server 70 follows path 208, then the healthcare facility has chosen to assign caregivers to specific patient support apparatuses 20. In such a facility, patient care server 70 proceeds from step 204 directly to step 214. At step 214, patient care server 70 sends a request to whichever server on network 72 contains the data correlating caregivers to patient support apparatuses 20. In the example shown in FIG. 3, patient support apparatus 20 contains table 130 that maps specific patient support apparatuses 20 to locations, and server 112 contains table 110 that maps locations to caregivers, so in this instance patient care server 70 is configured to send a request to both patient support apparatus server 132 and caregiver assignment server 112 in order to determine which caregivers are responsible for which individual patient support apparatuses 20. After obtaining these lists, patient care server 70 is able to determine what caregivers are assigned to what specific patient support apparatuses 20 at step 214, and patient care server 70 then proceeds to step 218.

If patient care server 70 follows path 210, then the healthcare facility has chosen to assign caregivers to specific patients. In such a facility, patient care server 70 proceeds from step 204 directly to step 216. At step 216, patient care server sends a request to ADT server 84 asking for the patient-room data contained within table 108. Patient care server also sends a request either to patient support apparatuses 20 themselves or patient support apparatus server 132 for the locations of each of the patient support apparatuses 20. Patient care server 70 also sends a request to caregiver assignment server 112 for the caregiver-patient assignments. After receiving this information, patient care server 70 proceeds to step 214 where it uses the caregiver-patient assignments and patient-room assignments to determine which caregivers are assigned to which rooms. Further, from this data and the patient support apparatus and room location data, patient care server 70 determines which caregivers are assigned to which patient support apparatuses 20. Patient care server 70 then proceeds to step 218.

Regardless of which path 206, 208, or 210 algorithm 154 follows, patient care server 70 determines at step 218 whether all of the patient support apparatuses 20 have been assigned to a caregiver or not. If they all have, patient care server 70 returns to step 200. If they have not, patient care server 70 proceeds to step 220 where it determines whether those patient support apparatuses 20 that have not been assigned to a caregiver are occupied or not. This may be done in the same manner discussed previously (e.g. by receiving data from load cells 54 and/or patient presence sensor(s) 62 onboard the patient support apparatuses 20 indicative of patient presence or absence). If the patient support apparatuses 20 that have not been assigned a caregiver are determined to be unoccupied at step 220, patient care server 70 returns back to step 200. If any of the patient support apparatuses 20 that have not been assigned a caregiver are occupied by a patient, as determined in step 220, patient care server 70 proceeds to step 222 and issues an alert.

The alert issued at step 222 (FIG. 7) is an alert indicating that there may be a patient within the healthcare facility who has not been assigned a caregiver, and therefore may accidentally be overlooked. The alert is sent in any of the same manners discussed above as the inactivity alerts are sent for algorithms 150 or 152. The alert notifies appropriate personnel that no caregiver has been assigned to a particular patient support apparatus 20, and therefore there is a possibility that the patient associated with that patient support apparatus 20 may not be properly looked after by a caregiver. Caregiver assignment monitoring algorithm 154 therefore provides a monitoring service that acts as a double check on the healthcare facility's caregiver assignment system to ensure that all patients are assigned a caregiver, or if they are not, appropriate personnel are notified. Algorithm 154 therefore helps reduce the possibility of a patient being overlooked. As noted above, algorithm 154 may run separately and/or in addition to any of the algorithms 150 and/or 152 executed by patient support apparatuses 20, and/or it may run separately or in addition to any of the other algorithms 156, 158, 270 and/or 300 that will be discussed in more detail below.

Figure 8:
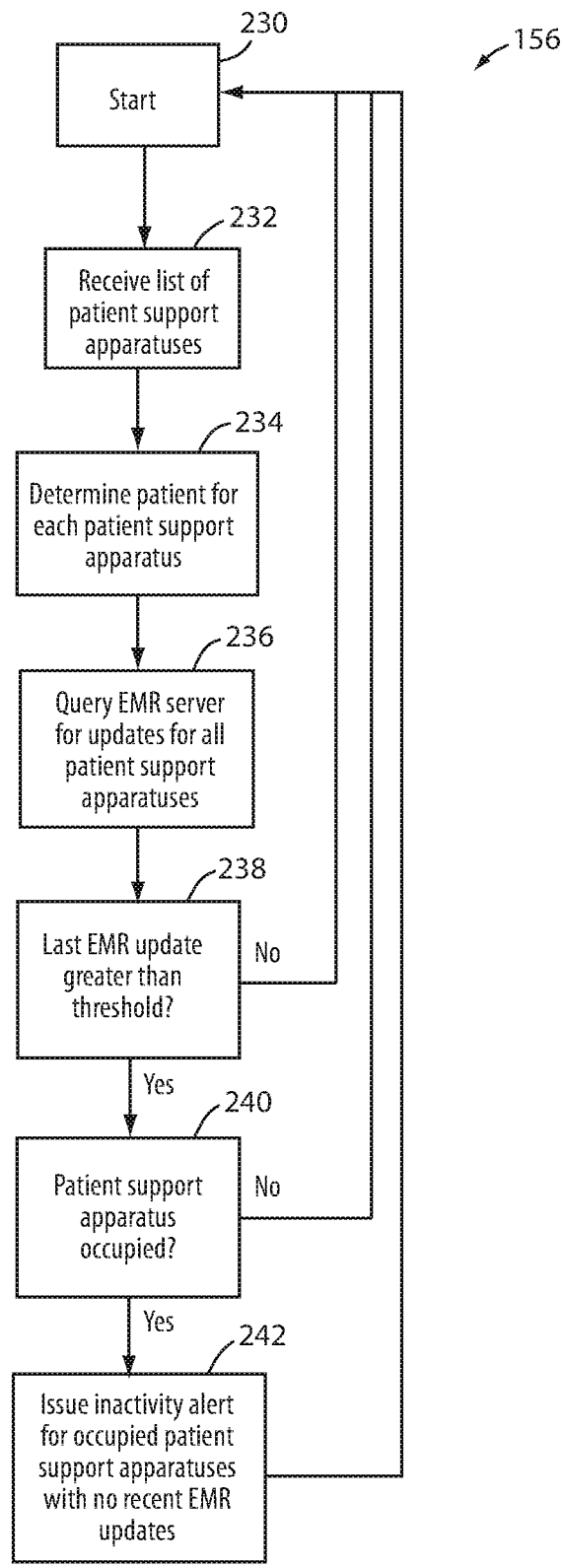
FIG. 8 is a flow chart of the Electronic Medical Records update monitoring algorithm of FIG. 4 executed by the patient care server of FIG. 3.

FIG. 8 depicts EMR update monitoring algorithm 156 according to one embodiment of the present disclosure. In general, EMR updating monitoring algorithm 156, which is executed by patient care server 70, monitors updates to the electronic medical records of patients and issues an alert if there are no such updates for a given patient for more than a set amount of time. Algorithm 156 therefore flags patients whose EMRs have not been recently updated so that caregivers are notified of such patients. The caregivers can then use these flagged patients to double check their care and make sure that the lack of EMR updates has not been due to oversight or neglect, or to correct such oversight or neglect before it becomes problematic. EMR update monitoring algorithm 156 therefore serves as yet another manner of helping to prevent unintentional neglect of patients within the healthcare facility.

EMR update monitoring algorithm 156 begins at step 230. Patient care server 70, in at least one embodiment, is configured to automatically and repetitively start algorithm 156 such that all of the patients within the healthcare facility have their EMR data monitored while in the healthcare facility. In other embodiments, patient care server 70 may be programmed to start at step 230 periodically, or it may be configured to begin execution in response to a manual command received from an authorized individual within the healthcare facility. In still other embodiments, algorithm 156 may be triggered by any combination of these events, or still other events.

After starting at step 230, patient care server 70 proceeds to step 232 where it receives a list of all of the patient support apparatuses 20 within the healthcare facility. Step 232 may be carried out in any of the same manners as step 202 of algorithm 154 discussed above. After retrieving this list at step 232, patient care server 70 proceeds to step 234 where it determines the patient that has been assigned to each patient support apparatus 20. This may be accomplished in different manners, depending upon how the particular healthcare facility assigns caregivers. In the example of FIG. 3, patient care server 70 obtains the location of patient support apparatuses 20 either directly from the patient support apparatuses 20 themselves, or from patient support apparatus server 132. Also in the example of FIG. 3, patient care server 70 obtains the patient-to-room assignments from ADT server 84. Using the location information of each patient support apparatus 20 and the identity of patients assigned to each location (from ADT server 84), patient care server is able to determine what patients have been assigned to what patient support apparatuses 20. After this determination is made, patient care server 70 proceeds to step 236.

At step 236 (FIG. 8), patient care server 70 queries EMR server 102 for any recent updates to the EMR of each patient who has been assigned to a patient support apparatus 20. After receiving this information, patient care server 70 proceeds to step 238 where it checks to see if the last EMR update has occurred within a threshold amount of time. The threshold used at step 238 may be configured and customized by authorized personnel of the healthcare facility and may be the same as, or different from, any of the other time thresholds discussed herein (e.g. the first or second thresholds used at steps 170 or 172 of algorithm 152). In some embodiments, the threshold may be on the order of 2-6 hours. However, in some embodiments, the threshold may be dynamic and automatically vary depending upon any one or more of the following: the particular patient (e.g. his or her diagnosis and/or prescribed treatment), the particular location of the patient (e.g. post-op locations versus normal acute care, etc.), the time of day (e.g. longer thresholds at night), and/or the content of the EMR update itself (e.g. some types of updates might correlate to different thresholds). Still other factors may be used for such dynamic thresholds.

If the EMR of a particular patient has been updated within the threshold period of time, as determined at step 238, patient care server 70 returns to step 230 and re-starts algorithm 156. If no EMR updates have been made within the threshold period of time, as determined at step 283 (FIG. 8), patient care server 70 proceeds to step 240. At step 240, patient care server 70 determines if the patient support apparatus 20 of the patient whose records have not been updated for longer than the threshold time period is currently occupying the patient support apparatus 20. If not, patient care server 70 returns back to step 230 and restarts algorithm 156. On the other hand, if the patient support apparatus 20 is occupied, as determined at step 240, patient care server 70 proceeds to step 242 where it issues an inactivity alert. The inactivity alert is issued and forwarded to the appropriate caregivers in any of the same manners discussed above with respect to the other inactivity alerts mentioned herein. As with all of the inactivity alerts, the inactivity alert issued at step 242 may be customized and/or configured in any of the manners discussed herein (e.g. targeted to specific caregivers, sent in a particular manner (e.g. email, text, voice, etc.), and/or otherwise customized). After issuing the alert at step 242, patient care server 70 returns back to step 230 and restarts algorithm 156.

As with all of the algorithms discussed herein, algorithm 156 may be modified in a number of different manners, including, but not limited to, re-ordering the steps shown in FIG. 8, adding one or more additional steps, and/or omitting one or more of the illustrated steps. As but one example, in some embodiments, algorithm 156 is modified to not inquire whether or not the patient support apparatuses are occupied or not, but instead issues an alert for any patient whose EMR has not been updated within the threshold amount of time, regardless of whether or not they are positioned on the patient support apparatus 20 or not (i.e. step 240 is omitted). In some such embodiments, algorithm 156 may be further modified to omit step 232 and/or 234, and simply check for EMR updates for all patients and issue an alert for those whose records have not been recently updated, regardless of the specific patient support apparatus that each patient has been assigned to. Still other variations are possible.

Figure 9:
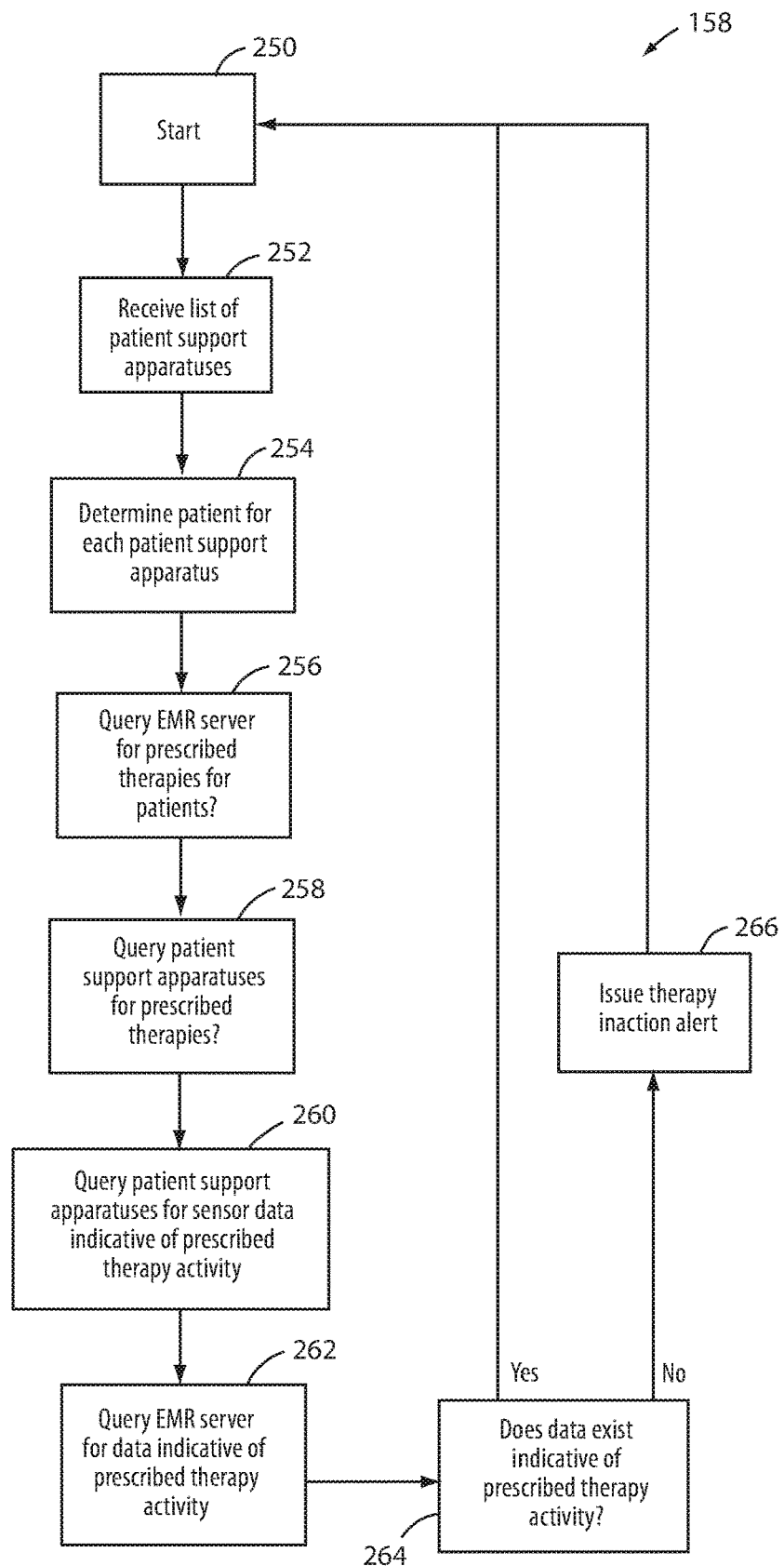
FIG. 9 is a flowchart of the prescribed therapy monitoring algorithm of FIG. 4 executed by the patient care server of FIG. 3.

FIG. 9 illustrates a prescribed therapy monitoring algorithm 158 according to one embodiment of the present disclosure. As with the other algorithms discussed herein, algorithm 158 may be executed by itself, or it may be executed in conjunction with one or more of the other algorithms. In general, prescribed therapy monitoring algorithm 158, which is executed by patient care server 70, examines the electronic medical records of a patient for prescribed therapies (including, but not limited to medications, treatments, and prescribed caregiver activities) and monitors updates to the electronic medical records of those patients to see if those prescribed therapies are completed within a timely manner. If they are not, patient care server 70 issues an alert. Algorithm 158 therefore flags patients whose EMRs have not been updated in a manner that matches what would be expected given the prescribed therapy for the patient. The caregivers can then use these flagged patients to either perform the neglected therapy or update the EMR to indicate that the prescribed therapy has been accomplished. In either case, prescribed therapy monitoring algorithm 158 therefore serves as yet another manner of helping to prevent overlooking patients and/or their treatment while staying within the healthcare facility.

Prescribed therapy monitoring algorithm 158 begins at a step 250. Step 250 may be triggered automatically and/or repetitively and/or in response to any of the triggering events discussed above with respect to algorithms 154 and/or 156. After step 250, patient care server 70 proceeds to step 252 where it receives a list of patient support apparatuses 20. Step 252 is the same as step 232 of algorithm 156, and therefore need not be discussed further. From step 252, patient care server 70 proceeds to step 254 where it determines which patient is assigned to each patient support apparatus 20. Step 254 is the same as step 234 discussed above with respect to algorithm 156, and therefore does not need to be described again.

After step 254, patient care server 70 proceeds to step 256 where it queries EMR server 102 for EMR records identifying any one or more of a plurality of prescribed actions for each of the patients. Although the term "prescribed therapy" is used herein, this term is not meant to exclude prescribed medications, prescribed treatments, prescribed testing, the measuring or monitoring of physiological characteristics, physical, occupational, or psychological therapy, the collection of other medical treatment data, and/or other types of activities that are prescribed or ordered by a caregiver. Examples of a prescribed therapy event include measuring selected physiological characteristics of the patient, such as respiratory function, blood glucose levels, blood pressure, heart rate, body weight, fluid intake and discharge rates, caloric intake, and any other medical treatment data collected from the patient. Other examples include performing an activity that is to be documented to the particular patient record stored in EMR server 102, such as, but not limited to, visiting the patient at a regular time interval, taking a weight reading of the patient; performing a fall risk or bed sore risk assessment of the patient, etc. The prescribed therapies refer to not only therapies that are individually prescribed for a particular patient, but also therapies and/or protocols that are generally applicable to all patients within the healthcare facility (and/or all patients within a particular location in the facility, and/or all patients that have been diagnosed with a particular condition, etc.).

After obtaining the prescribed therapy information from EMR server 102 at step 256, patient care server 70 proceeds to step 258 where is queries the patient support apparatuses 20 for any prescribed therapies that have been input into patient support apparatus 20 (and which may not be reflected in the records stored in EMR server 102). For example, in some instances, the prescribed therapy may prescribe that a patient be turned every so often, and a turning schedule may be input into the memory of the patient support apparatus 20. Other therapy prescriptions may also be input into the patient support apparatus 20, such as, but not limited to, a weighing schedule, a mobility schedule (e.g. a prescribed amount of time that the patient exits from patient support apparatus 20), a mattress therapy, etc. Any such therapies that have been input into patient support apparatus 20 are sent to patient care server at step 258.

After querying patient support apparatuses 20 at step 258 for prescribed therapies, patient care server 70 proceeds to step 260 where it queries the patient support apparatuses 20 for information indicating that one or more of the prescribed therapies (whether stored on the patient support apparatus 20 or in the EMR) have been accomplished. For example, in some instances, the prescribed therapy may prescribe that a patient be turned every so often, and patient support apparatuses 20 are configured to detect such turning. If such a turning protocol has been instituted for a particular patient, patient care server 70 queries the patient support apparatus 20 for that particular patient at step 258 to see if the patient has, in fact, been turned. Patient care server 70 also queries the patient support apparatus 20 for any and all other prescribed therapies that can be detected by the patient support apparatus 20 (e.g. weighing the patient, transferring the patient, etc.). After receiving any information from patient support apparatuses 20 that would indicate the successful completion one or more prescribed therapies, patient care server 70 proceeds to step 262.

At step 262, patient care server 70 queries the EMR server 102 to see if there are updates to the EMR records indicating that the prescribed therapies have been completed within either a prescribed time period, or an acceptable time window. The acceptable time window may be customized and/or configured by authorized healthcare personnel and may vary for different prescribed therapies. For example, a prescription to have an X-ray taken may be assigned a time threshold different than, say, a prescription to have a vital sign reading taken from the patient. At step 264, patient care server 70 determines if data exists indicating that the prescribed therapies have taken place within the prescribed time window or the acceptable time window. If they have not, patient care server 70 proceeds to step 266 and issues a therapy inaction alert. The therapy inaction alert may be issued in any of the same manners described above for any of the other alerts (e.g. the inactivity alert of algorithms 150, 152, etc.). If patient care server 70 determines at step 264 that the data indicates that the prescribed therapy has been completed, or the prescribed or acceptable time period has not yet expired, it returns to step 250. Algorithm 158 therefore serves as an automated monitoring system that helps ensure that prescribed actions are taken in a timely manner and, if they are not, alerts are automatically issued to the appropriate personnel within the healthcare facility.

Figure 10:
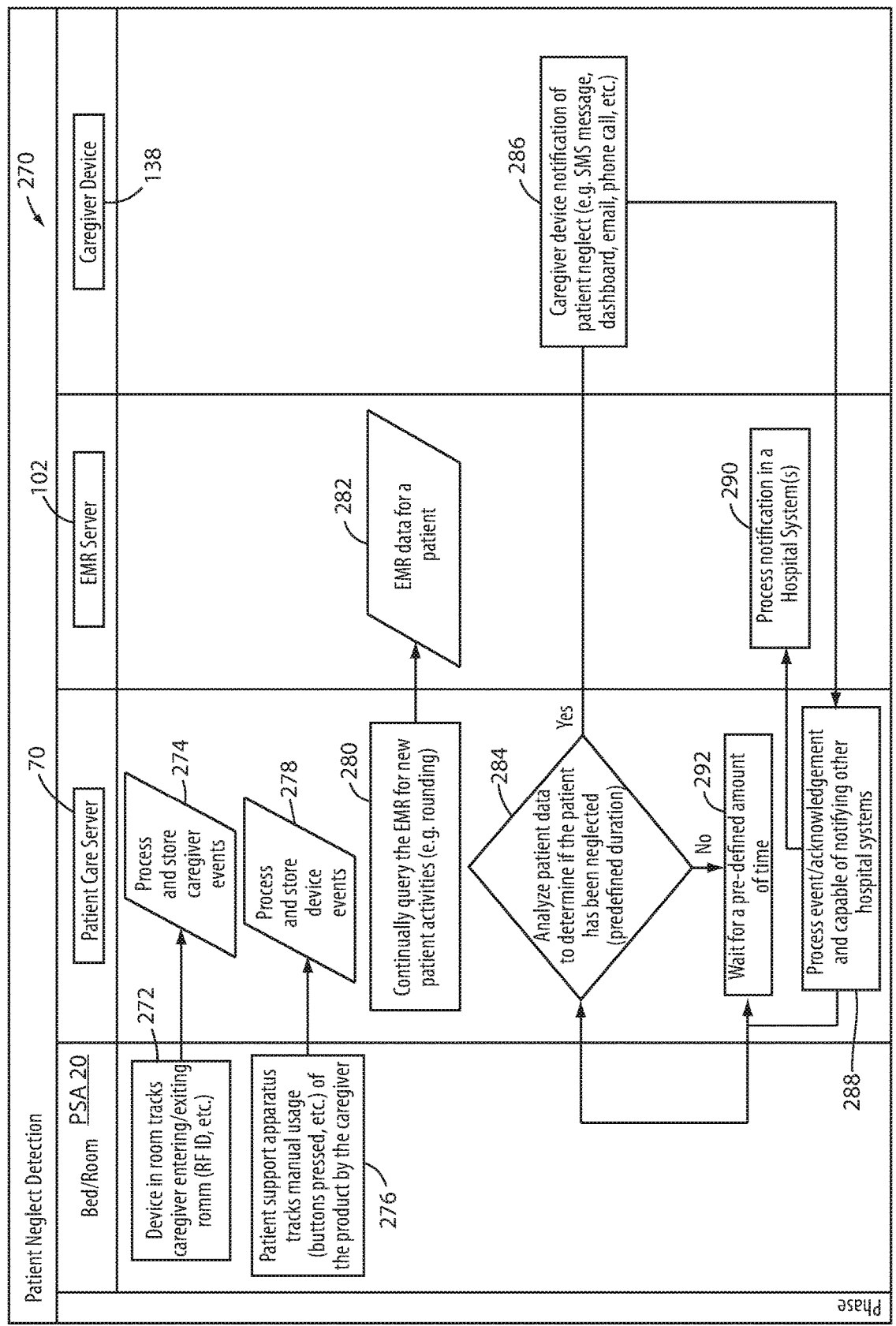
FIG. 10 is a flowchart of a patient neglect detection algorithm executed by various components of another embodiment of the patient care system of the present disclosure.

FIG. 10 illustrates a patient neglect algorithm 270 according to another embodiment of the present disclosure. Patient neglect algorithm 270 may be executed in combination with any one or more of the algorithms previously described herein, or it may be executed by itself. As will be apparent from the following discussion, patient neglect algorithm 270 combines together some aspects from multiple ones of the algorithms previously discussed.

Patient neglect algorithm 270 includes one or more steps that are executed on patient support apparatuses 20, one or more steps that are executed on patient care server 70, one or more steps that are executed on EMR server 102, and one or more steps that are executed on one or more of the mobile electronic devices 138 carried by caregivers. Turning first to the steps executed on the patient support apparatuses 20, controller 58 of patient support apparatuses 20 detects if a caregiver is present adjacent to patient support apparatus 20 (e.g. within the same room) at a step 272. Step 272 is carried out using one or more of caregiver presence sensors 144. Controller 58 of patient support apparatus 20 reports to patient care server 70 whether a caregiver is detected or not at step 272. At step 274, patient care server 70 receives those results and stores them in memory, including a time stamp of the results. At step 276, controller 58 of patient support apparatus 20 also detects whether a caregiver is using patient support apparatus 20. This step is carried out in the same manner as steps 164 and 166 of algorithm 152. That is, controller 58 checks to see if any of the controls on any of the caregiver control panels 48a or 48c have been activated, or if a caregiver has made audio contact with the patient via the nurse call functionality built into the patient support apparatus 20 (e.g. nurse call button 90, speaker 96, and microphone 88). Controller 58 reports the results of step 276 to patient care server 70 and patient care server 70 stores these results, including a time stamp, at step 278.

Patient care server 70 also repetitively queries EMR server 102 at step 280 for new patient activities (e.g. updates), such as, but not including, rounding (FIG. 10). At step 282, EMR server 102 reports such new updates, if any, to patient care server 70. At step 284, patient care server 70 analyzes the EMR data received both from the patient support apparatuses 20 and from EMR server 102 in order to determine if the patient is potentially being neglected or not. This analysis is carried out in the same manner as the analyses of steps 168-174 of algorithm 152 and steps 238-242 of algorithm 156, in at least one embodiment. That is, patient care server 70 determines if the caregiver's presence at the patient support apparatus 20 has either been directly detected by caregiver presence sensors 144, or indirectly detected by usage of one of the caregiver control panels within a threshold period of time. It also determines if the patient has communicated with the caregiver more recently than a threshold period of time. Still further, it analyzes the EMR records to see if they have been updated within another threshold amount of time. If the caregiver hasn't been recently (i.e. within the time threshold) detected at the patient support apparatus 20, and the caregiver hasn't recently communicated with the patient via the nurse call functionality, and the patient's EMR records have not been updated recently, then patient care server 70 determines that the patient may be experiencing neglect, and it proceeds to step 286. It will be understood that in carrying out this analysis, different thresholds may be used when examining each of the different data points in step 284, and that such thresholds may vary based upon any of the factors discussed above (e.g. whether the patient is asleep, the time of day, the location of the patient support apparatus 20, the diagnosis of the patient, the specific type of EMR update, etc.). In other words, the thresholds used in step 284 may correspond to any of the various thresholds previously described, and their variants, with respect to algorithms 152 and/or 156.

At step 286 (FIG. 10), the caregiver's portable electronic device 138 receives a text, email, phone call, or other notification that a particular patient may be being neglected. As noted previously, the communication to electronic device 138 is sent by patient care server 70 in some embodiments, while in other embodiments it may be sent by an intermediary server in response to a message from patient care server 70. The caregiver's portable electronic device 138 is in communication with network 72 and patient care server 70. In response to the alert received at step 286, the caregiver is therefore able to send a reply and/or acknowledgement back to patient care server 70. This reply/acknowledgement is received by patient care server 70 at step 288. In some embodiments, the reply/acknowledgement may include a message indicating that the patient has been checked on, that his or her EMR record has been updated, or that the caregiver has taken some other action to remedy the cause of the alert. In such embodiments, patient care server 70 is configured to send a message to the EMR server 102 at step 290 indicating that such a remedy has taken place. Alternatively, patient care server 70 is configured to send a message at step 288 to EMR server 102 that indicates that the caregiver has acknowledged the alert message. EMR server 102 stores whatever message it receives, and its contents, at step 290. After sending the message at step 288, patient care server 70 returns to step 284 and carries out the previously described analyses using fresh data from the patient support apparatus 20 and EMR server 102, as well as one or more reset timers used for determining the various time thresholds utilized in step 284.

If patient care server 70 determines at step 284 that no cause for an alert exists, it proceeds to step 292 where it waits for a predefined amount of time. After waiting for the predefined amount of time, patient care server 70 returns to step 284 and carries out the previously described analyses using fresh data from the patient support apparatus 20 and EMR server 102, but not any reset timers. Depending upon the outcome of that analyses, patient care server 70 then proceeds to either step 286 or step 292 and follows those steps in the manners previously described.

As with all of the algorithms described herein, algorithm 270 may be modified in a number of different manners, including, but not limited to, re-ordering any of the steps shown in FIG. 10, adding one or more additional steps, omitting one or more of the illustrated steps, and/or changing the device that performs one or more of the steps. As but one example, in some embodiments, algorithm 270 is modified to offload some, or all, of the computations carried out by patient care server 70 to the mobile electronic devices 138 carried by the caregivers. In such embodiments, mobile device 138 carries out the analysis of step 284. Further, in some such embodiments, the mobile device 138 may communicate directly with EMR server 102 and/or patient support apparatuses 20 directly, thereby avoiding the need for patient care server to act as an intermediary. Indeed, in at least one embodiment, patient care server 70 is omitted and the functions of the patient care server 70 are performed by mobile electronic devices 138 and/or patient support apparatuses 20. Still other variations are possible.

Figure 11:
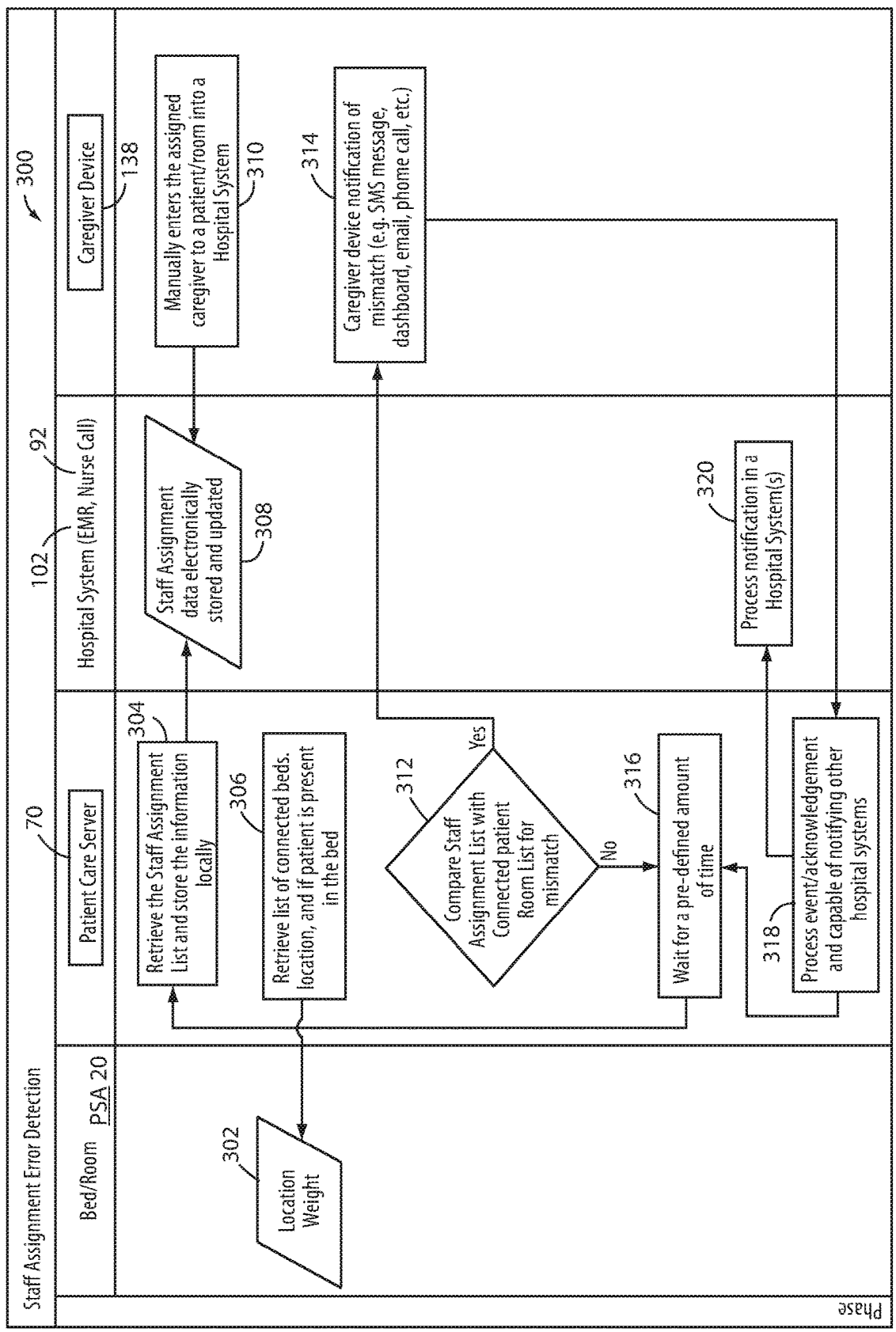
FIG. 11 is a flowchart of a staff assignment error algorithm executed by various components of yet another embodiment of the patient care system of the present disclosure.

FIG. 11 illustrates a staff assignment error detection algorithm 300 according to another embodiment of the present disclosure. Staff assignment error detection algorithm 300 may be executed in combination with any one or more of the algorithms previously described herein, or it may be executed by itself. As will be apparent from the following discussion, staff assignment error detection algorithm 300 performs a function similar to that of caregiver assignment monitoring algorithm 154 and uses one or more steps that are similar to those of algorithm 154.

Staff assignment error detection algorithm 300 includes one or more steps that are executed on patient support apparatuses 20, one or more steps that are executed on patient care server 70, one or more steps that are executed on EMR server 102, and one or more steps that are executed on one or more of the mobile electronic devices 138 carried by caregivers. Staff assignment error detection algorithm 300 begins at step 302 where controller 58 of patient support apparatus 20 determines if a patient is present on the patient support apparatus 20 by determining if the amount of weight detected load cells 54 is greater than a threshold. Step 302 may be modified and/or supplemented in a variety of different manners. For example, one or more patient detection sensors 62 may be utilized to determine if the patient is present or not, either alone or in addition to the load cell readings. Regardless of the specific sensors used, controller 58 of patient support apparatus 20 sends a message to patient care server 70 indicating whether the patient is present or not.

Patient care server 70 retrieves a list of caregiver assignments at step 304 of algorithm 300 (FIG. 11). In some embodiments, these are retrieved in the same manner as steps 204-216 of algorithm 154. In other embodiments, the retrieval of the caregiver assignments may be carried out in other manners. As shown in FIG. 11, the caregiver assignment data is stored electronically on one or more servers on network 72 at step 308. These servers include, but are not limited to, the EMR server 102 and the nurse call server 92. The caregiver assignment data may be entered using one or more of the caregiver's mobile electronic devices 138, as indicated at step 310. Other devices may also or additionally be used to enter the caregiver assignment data.

After retrieving the list of caregiver assignments at step 304, patient care server 70 proceeds to step 306 where it retrieves a list of connected patient support apparatuses 20, their locations, and information indicating whether the patient is currently occupying the patient support apparatus 20 or not. The list of connected patient support apparatuses 20 is retrieved, in some embodiments, in any of the manners that step 202 of algorithm 154 is carried out, as was previously discussed. Other manners can, of course, be used. The location of the patient support apparatuses 20 may be determined in the same manner as step 212 of algorithm 154, or it may be carried out in other manners. The data indicating whether the patient support apparatuses 20 are occupied or not comes directly from the patient support apparatuses 20 via step 302, described above.

After receiving the information of step 306, patient care server 70 proceeds to step 312 where it determines if there are any mismatches between the occupied patient support apparatuses 20 and the caregiver assignments, particularly any occupied patient support apparatuses 20 that do not have a caregiver assigned to them. Step 312, in some embodiments, is carried out in the same manner as steps 218 and 220 of algorithm 154, as described above. If there is any mismatch, patient care server 70 sends a message to the appropriate caregiver mobile electronic device 138, as indicated at step 314. This alert message may be accomplished in the same manner as step 222 of algorithm 154. If no mismatch is detected at step 312, patient care server 70 proceeds to step 316 where it waits for a predefined amount of time before returning to steps 304, 306, and 312. When patient care server 70 gets to step 312 after completing step 316 (i.e. after completing steps 304 and 306 again), it performs step 312 again using a fresh set of data (i.e. a fresh list of caregiver assignments, a fresh list of occupied patient support apparatuses 20, and a fresh listing of the locations of those patient support apparatuses 20). This fresh data is retrieved when steps 304 and 306 are repeated, and patient care server 70 uses this fresh data to perform a new analysis at step 312.

If an alert is sent out to one of more of the caregivers' mobile electronic devices 138, as indicated at step 314 (FIG. 11), the mobile electronic devices 138 are configured to allow the caregiver to correct the mismatch and/or acknowledge the alert message. When taking either of these actions, the mobile electronic device 138 sends a message back to patient care server 70 that is received and processed at step 318. Patient care server 70 is configured to send a message to the EMR server 102 and/or the nurse call server 92 (or whatever server stores the caregiver assignment data) at step 320 indicating that the mismatch has been acknowledged and/or corrected. The recipient server stores this message and its contents. After sending the message at step 318, patient care server 70 proceeds to step 316 and waits for a predefined amount of time before returning back to step 304 in the manner previously described.

In any of the algorithms described above that monitor patient-caregiver interactions, such algorithms may be modified and/or supplemented with data obtained from caregiver tracking server 122. As noted, tracking server 122 receives real time caregiver location data and transmits the caregiver location data to patient care server 70. The caregiver location data indicates the location of caregivers within the healthcare facility. Patient care server 70 also receives the location of each particular patient support apparatus 20 within the healthcare facility, as noted. The patient care server 70 can utilizes the patient support apparatus location data and the caregiver location data to determine if a caregiver has visited a particular location within the healthcare facility within a predetermined amount of time. The patient care server 70 issues an inactivity alert if a caregiver has not visited the location of an occupied patient support apparatus within one of the threshold amounts of time.

It will be understood that any of the features, functions, and/or steps of any of the algorithms discussed herein may be combined with any of the features, functions, and/or steps of any of the other algorithms described herein.

The various embodiments of the patient care system 106 described herein are configured to help healthcare facility staff reduce or avoid caregiver assignment errors and caregiver inattention issues, which may lead to patient neglect. The system generates and issues alerts when such errors or issues are identified. For example, an alert may be issued when a patient has not been attended to by a caregiver within a period of time greater than a certain period, or when a caregiver has not been assigned to a particular location within the healthcare facility to which a patient has been assigned. The patient support apparatus communicates with multiple other conventional healthcare facility systems and devices to gather and share information and data to help caregivers avoid neglecting a patient.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus system for use within a healthcare facility comprising:
   a patient support apparatus comprising:
      a litter frame;
      a support deck supported on the litter frame and adapted to support a patient thereon;
      a sensor adapted to detect a presence of the patient;
      a transceiver; and
      a controller in communication with the sensor and the transceiver; and
   a server in communication with the patient support apparatus via the transceiver, the server further being in communication with an admission/discharge/tracking (ADT) server that stores a location assignment for the patient, the server configured to receive location data regarding a current location of the patient support apparatus, to use the current location of the patient support apparatus and the location assignment for the patient to determine if a caregiver has been assigned to the current location of the patient support apparatus, and to issue an alert if the server determines that a caregiver has not been assigned to the current location of the patient support apparatus.

2. The patient support apparatus system of claim 1 wherein the server is further configured to not issue the alert if the sensor detects that a patient is not present on the support deck.

3. The patient support apparatus system of claim 1 wherein the server is further configured to communicate with a caregiver assignment server that stores caregiver assignments to locations within the healthcare facility, and to use the caregiver assignments to determine if a caregiver has been assigned to the current location of the patient support apparatus.

4. The patient support apparatus system of claim 1 wherein the patient support apparatus includes a location detector adapted to receive a location identifier from a fixed locator when the patient support apparatus is positioned adjacent the fixed locator.

5. The patient support apparatus system of claim 4 wherein the controller is adapted to transmit the location identifier to the server, and the location identifier provides location data regarding the current location of the patient support apparatus.

6. The patient support apparatus system of claim 5 wherein the current location of the patient support apparatus is a room within the healthcare facility.

7. The patient support apparatus system of claim 3 wherein the patient support apparatus includes a location detector adapted to receive a location identifier from a fixed locator when the patient support apparatus is positioned adjacent the fixed locator, and
   wherein the server is configured to receive caregiver location data from a real time locating and tracking server indicating locations of caregivers within the healthcare facility, the server further adapted to use the location data to determine if a caregiver has visited a location within the healthcare facility corresponding to the location identifier within a predetermined amount of time and to issue an inactivity alert if a caregiver has not visited the location corresponding to the location identifier within the predetermined amount of time.

8. The patient support apparatus system of claim 7, wherein the patient support apparatus further comprises a clock and the predetermined amount of time is based on a time of day.

9. The patient support apparatus system of claim 8 further comprising a sleep sensor adapted to sense a patient's sleep state and to communicate the sleep state to the controller, wherein the predetermined amount of time is based on the patient's sensed sleep state.

10. The patient support apparatus system of claim 7 wherein the predetermined amount of time does not start until a patient's presence is detected on the support deck.

11. A patient support apparatus system for a healthcare facility comprising:
   a patient support apparatus comprising:
      a litter frame;
      a support deck supported on the litter frame and adapted to support a patient thereon;
      a location detector adapted to receive a location identifier from a fixed locator when the patient support apparatus is positioned adjacent the fixed locator;
      a transceiver; and
      a controller adapted to transmit the location identifier; and a server adapted to receive the location identifier from the patient support apparatus and correlate the location identifier with a location within the healthcare facility, the server adapted to receive caregiver location data from a real time locating and tracking server indicating locations of caregivers within the healthcare facility, the server further adapted to use the location data to determine if a caregiver has visited a location within the healthcare facility corresponding to the location identifier within a predetermined amount of time and to issue an inactivity alert if a caregiver has not visited the location corresponding to the location identifier within the predetermined amount of time.

12. The patient support apparatus system of claim 11 wherein the locating and tracking server is adapted to track caregiver location badges worn by caregivers.

13. The patient support apparatus system of claim 11 wherein the patient support apparatus includes a sensor adapted to detect a presence of a patient.

14. The patient support apparatus system of claim 13 wherein an inactivity alert is not sent if the patient is not determined by the sensor to be present on the patient support apparatus.

15. The patient support apparatus system of claim 13, the patient support apparatus further comprising a clock in communication with the controller, wherein the predetermined amount of time is based on a time of day.

16. The patient support apparatus system of claim 13, the patient support apparatus further comprising a sleep sensor adapted to sense a patient's sleep state, the sleep sensor in communication with the controller, wherein the predetermined amount of time is based on the patient's sensed sleep state.

17. The patient support apparatus system of claim 12 the server further being in communication with an electronic medical records (EMR) server that stores patient records, the server configured to retrieve a particular patient record from the EMR server corresponding to the patient to determine if updates to the particular patient record have occurred within the predetermined amount of time, and to issue an inactivity alert if the particular patient record has not been updated within the predetermined amount of time.

18. The patient support apparatus system of claim 12 the server further being in communication with an admission/discharge/tracking (ADT) server that stores patient location information, the server configured to receive location data regarding a current location of the patient to determine if a caregiver has been assigned to the current location of the patient, and to issue an alert if the server determines that a caregiver has not been assigned to the current location of the patient.

19. The patient support apparatus system of claim 12 further comprising a timer in communication with the controller,
wherein the controller is configured to send a caregiver inactivity message to the server when caregiver activity has not been detected for a period of time greater than a predetermined period of time.

20. The patient support apparatus system of claim 12 further comprising a caregiver control panel in communication with the controller,
wherein the controller is adapted to send a caregiver activity message to the server in response to any control on the caregiver control panel being activated.

* * * * *